United States Patent
Kshirsagar et al.

(10) Patent No.: US 9,328,325 B2
(45) Date of Patent: May 3, 2016

(54) SAMPLING DEVICES AND METHODS FOR CONCENTRATING MICROORGANISMS

(75) Inventors: Manjiri T. Kshirsagar, Woodbury, MN (US); Kurt J. Halverson, Lake Elmo, MN (US); Neil Percy, St. Paul, MN (US); James E. Aysta, Stillwater, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 587 days.

(21) Appl. No.: 13/142,288

(22) PCT Filed: Dec. 30, 2009

(86) PCT No.: PCT/US2009/069780
§ 371 (c)(1),
(2), (4) Date: Sep. 21, 2011

(87) PCT Pub. No.: WO2010/078399
PCT Pub. Date: Jul. 8, 2010

(65) Prior Publication Data
US 2012/0003626 A1   Jan. 5, 2012

Related U.S. Application Data

(60) Provisional application No. 61/141,900, filed on Dec. 31, 2008.

(51) Int. Cl.
*B01D 21/00* (2006.01)
*B01D 21/01* (2006.01)
*C12M 1/00* (2006.01)
*G01N 1/40* (2006.01)

(52) U.S. Cl.
CPC ............... *C12M 47/02* (2013.01); *G01N 1/40* (2013.01); *G01N 1/405* (2013.01); *G01N 2001/4088* (2013.01)

(58) Field of Classification Search
USPC ........................................... 435/288.5
See application file for complete search history.

(56) References Cited

U.S. PATENT DOCUMENTS 3,481,712 A   12/1969   Bernstein et al.
3,656,912 A * 4/1972   Sugawara ............ 422/533

(Continued)

FOREIGN PATENT DOCUMENTS

CN   101052866 A   10/2007
CN   2844887 Y    12/2008

(Continued)

OTHER PUBLICATIONS

Lukasik et al. 1996 (Adsorption of Microorganisms to Sand and Diatomaceous Earth Particles Coated with Metallic Hydroxides; KONA 14:87-91).*

(Continued)

*Primary Examiner* — Gary Nickol
*Assistant Examiner* — Mary Lyons

(57) ABSTRACT

The present disclosure describes methods for concentrating microorganisms with concentration agents in a sampling device and the sampling device described herein. More specifically, methods for concentrating microorganisms from large volume samples with concentration agents in a sampling device can provide for rapid, low cost, simple (involving no complex equipment or procedures), and/or effective processes under a variety of conditions.

13 Claims, 6 Drawing Sheets

(56) References Cited

U.S. PATENT DOCUMENTS

| | | | |
|---|---|---|---|
| 3,745,090 | A | 7/1973 | Chappelle et al. |
| 3,836,334 | A * | 9/1974 | Karamian ................. 422/533 |
| 3,897,902 | A | 8/1975 | Yanez, Jr. |
| 3,933,592 | A | 1/1976 | Clendenning |
| 3,971,703 | A | 7/1976 | Picciolo et al. |
| 4,144,134 | A | 3/1979 | Plakas |
| 4,303,752 | A | 12/1981 | Kolehmainen et al. |
| 4,421,848 | A | 12/1983 | Whitlock |
| 4,503,149 | A | 3/1985 | Boyd |
| 4,698,311 | A | 10/1987 | Hall et al. |
| 4,729,846 | A | 3/1988 | Matsui et al. |
| 4,906,565 | A | 3/1990 | Vossen |
| 5,238,812 | A | 8/1993 | Coulter et al. |
| 5,258,285 | A | 11/1993 | Aegidius |
| 5,264,184 | A | 11/1993 | Aysta et al. |
| 5,576,185 | A | 11/1996 | Coulter et al. |
| 5,595,653 | A | 1/1997 | Good et al. |
| 5,695,989 | A | 12/1997 | Kalamasz |
| 5,891,702 | A | 4/1999 | Sakakibara et al. |
| 5,905,029 | A | 5/1999 | Andreotti et al. |
| 5,908,751 | A | 6/1999 | Higo et al. |
| 6,045,913 | A | 4/2000 | Castle |
| 6,140,040 | A | 10/2000 | Palm et al. |
| 6,174,704 | B1 | 1/2001 | Chu et al. |
| 6,200,767 | B1 | 3/2001 | Sakakibara et al. |
| 6,451,260 | B1 | 9/2002 | Düsterhöft et al. |
| 6,465,201 | B1 | 10/2002 | Presente et al. |
| 6,588,681 | B2 | 7/2003 | Rothrum et al. |
| 6,660,489 | B2 | 12/2003 | Schrecengost et al. |
| 6,824,560 | B2 | 11/2004 | Pelton |
| 6,861,067 | B2 | 3/2005 | McGhee et al. |
| 6,967,261 | B1 | 11/2005 | Soerens et al. |
| 7,005,143 | B2 | 2/2006 | Abuelyaman et al. |
| 7,045,913 | B2 | 5/2006 | Ebrahim et al. |
| 7,083,911 | B2 | 8/2006 | Wood et al. |
| 7,141,033 | B2 | 11/2006 | Kanjilal et al. |
| 7,282,181 | B2 | 10/2007 | Hudak et al. |
| 7,338,692 | B2 | 3/2008 | Smith et al. |
| 7,422,868 | B2 | 9/2008 | Fan et al. |
| 7,485,609 | B2 | 2/2009 | Reddy et al. |
| 7,553,417 | B2 | 6/2009 | Waller, Jr. et al. |
| 7,824,732 | B2 | 11/2010 | Sahouani et al. |
| 2003/0104507 | A1 | 6/2003 | Wood et al. |
| 2003/0140785 | A1* | 7/2003 | Koslow ........................... 95/90 |
| 2004/0157971 | A1 | 8/2004 | Kim |
| 2004/0161788 | A1 | 8/2004 | Chen et al. |
| 2004/0197845 | A1 | 10/2004 | Hassibi et al. |
| 2005/0048592 | A1 | 3/2005 | Wood et al. |
| 2005/0070701 | A1 | 3/2005 | Hochstetler et al. |
| 2005/0142571 | A1 | 6/2005 | Parthasarathy et al. |
| 2005/0152992 | A1 | 7/2005 | Johnson, Jr. et al. |
| 2005/0153423 | A1 | 7/2005 | Baba et al. |
| 2005/0181467 | A1 | 8/2005 | Schrecengost et al. |
| 2005/0250138 | A1 | 11/2005 | Young et al. |
| 2006/0062854 | A1 | 3/2006 | Chandra et al. |
| 2006/0166347 | A1 | 7/2006 | Faulstich et al. |
| 2006/0273049 | A1 | 12/2006 | Leach et al. |
| 2007/0062870 | A1* | 3/2007 | Chen et al. ..................... 210/636 |
| 2007/0148458 | A1 | 6/2007 | Sahouani et al. |
| 2007/0212266 | A1 | 9/2007 | Johnston et al. |
| 2007/0269341 | A1 | 11/2007 | Halverson et al. |
| 2008/0023408 | A1 | 1/2008 | Hansen |
| 2008/0064939 | A1 | 3/2008 | Reynolds et al. |
| 2008/0153125 | A1 | 6/2008 | Buttry et al. |
| 2008/0207794 | A1 | 8/2008 | Wright et al. |
| 2009/0068065 | A1 | 3/2009 | Pagoria et al. |
| 2010/0190171 | A1 | 7/2010 | Kshirsagar et al. |
| 2010/0209927 | A1 | 8/2010 | Menon et al. |
| 2010/0209961 | A1 | 8/2010 | Kshirsagar et al. |
| 2010/0248214 | A1 | 9/2010 | Kshirsagar et al. |
| 2012/0009588 | A1* | 1/2012 | Rajagopal et al. ........... 435/6.15 |

FOREIGN PATENT DOCUMENTS

| | | |
|---|---|---|
| DE | 1 442 223 | 11/1969 |
| EP | 1 845 375 | 10/2007 |
| GB | 2 138 021 | 10/1984 |
| GB | 2 433 219 | 6/2007 |
| JP | 7-509369 | 10/1995 |
| JP | 2005-515892 | 6/2005 |
| JP | 2005-254123 | 9/2005 |
| JP | 2008-136440 | 6/2008 |
| JP | 2008-220319 | 9/2008 |
| WO | WO 89/09279 | 10/1989 |
| WO | WO 8909279 A1 * | 10/1989 |
| WO | WO 93/00994 | 1/1993 |
| WO | WO 94/03645 | 2/1994 |
| WO | WO 97/02812 | 1/1997 |
| WO | WO 00/29112 | 5/2000 |
| WO | WO 03/064330 | 8/2003 |
| WO | WO 2005/094792 | 10/2005 |
| WO | WO 2006/007711 | 1/2006 |
| WO | WO 2006/072944 | 7/2006 |
| WO | WO 2007/113583 | 10/2007 |
| WO | WO 2007/137257 | 11/2007 |
| WO | WO 2007137257 A2 * | 11/2007 |
| WO | WO 2007/146722 | 12/2007 |
| WO | WO 2008/075044 | 6/2008 |
| WO | WO 2008/117052 | 10/2008 |
| WO | WO 2008/122908 | 10/2008 |
| WO | WO 2008/129517 | 10/2008 |
| WO | WO 2008/134472 | 11/2008 |
| WO | WO 2008/150779 | 12/2008 |
| WO | WO 2009/009188 | 1/2009 |
| WO | WO 2009/046081 | 4/2009 |
| WO | WO 2009/046183 | 4/2009 |
| WO | WO 2009/046191 | 4/2009 |
| WO | WO 2009/048743 | 4/2009 |
| WO | WO 2009/061864 | 5/2009 |
| WO | WO 2009/067498 | 5/2009 |
| WO | WO 2009/067503 | 5/2009 |
| WO | WO 2009/067513 | 5/2009 |
| WO | WO 2009/067518 | 5/2009 |
| WO | WO 2009/076267 | 6/2009 |
| WO | WO 2009/082667 | 7/2009 |
| WO | WO 2009/085357 | 7/2009 |
| WO | WO 2009/102859 | 8/2009 |
| WO | WO 2009/137138 | 11/2009 |
| WO | WO 2010/039627 | 4/2010 |
| WO | WO 2010/078404 | 7/2010 |
| WO | WO 2010/078482 | 7/2010 |
| WO | WO 2010/129726 | 11/2010 |
| WO | WO 2010/129727 | 11/2010 |
| WO | WO 2010/129728 | 11/2010 |
| WO | WO 2011/079038 | 6/2011 |
| WO | WO 2011/082309 | 7/2011 |

OTHER PUBLICATIONS

Berry, E.D. et al.; "Hydroxyapatite Adherence as a Means to Concentrate Bacteria"; Applied and Environmental Microbiology; vol. 63, No. 10; 1997; pp. 4069-4074.

DeLuca, M. et al.; "Factors Affecting the Kinetics of Light Emission from Crude and Purified Firefly Luciferase"; Analytical Biochemistry; vol. 95; 1979; pp. 194-198.

Gorus, F. et al.; "Applications of Bio- and Chemiluminescence in the Clinical Laboratory"; Clinical Chemistry; vol. 25, No. 4; 1979; pp. 512-519.

Harvey, E.N. "A History of Luminescence—From the Earliest Times Until 1900"; American Philosophical Society, Philadelphia, PA 1957 (cover, copyright, and Table of Contents consisting of 12 pgs).

Lee JiYoung et al.; "Detection of E. coil in beach water within 1 hour using immunomagnetic separation and ATP bioluminescence"; Luminescence; vol. 19, No. 1; 2004; pp. 31-36.

McElroy, W.D. et al.; "Factors Influencing the Response of the Bioluminescent Reaction to Adenosine Triphosphate"; Archives of Biochemistry; vol. 22; 1949; pp. 420-433.

Morbe, J.L. et al.; "Release of miniantibodies from E. coli cells into the supernatant at low and high cell densities": Micorbiol. Res.; vol. 152; No. 4; 1997; pp. 385-394.

(56) References Cited

OTHER PUBLICATIONS

Navrátil, M. et al.; "Chapter 34—Bioluminescence in Immobilized Cells for Biomass Detection and Biosensor Applications"; Methods in Biotechnology: Immobilization of Enzymes and Cells, Second Edition; vol. 22; 2006; pp. 393-401.

Oster, J., et al.; "Polyvinyl-alcohol-based magnetic beads for rapid and efficient separation of specific or unspecific nucleic acid sequences"; Journal of Magnetism and Magnetic Materials; vol. 225; 2001; pp. 145-150.

Stanley, P.E.; "[2] Extraction of Adenosine Triphosphate from Microbial and Somatic Cells"; Methods in Enzymology; vol. 133; Bioluminescence and Chemiluminescence Part B; 1986; pp. 14-22.

Abstract entitled "Waterborne *Cryptosporidium parvum* detection using the particle filtration system and quantitative PCR"; from General Meeting of the American Society for Microbiology; vol. 103; 2003; p. Q-096.

Abstract entitled "Use of fluorescent microspheres to evaluate the particle filtration system for waterborne pathogen detection"; from General Meeting of the American Society for Microbiology; vol. 103; 2003; pp. Q-268.

"Standard Methods for the Examination of Water and Wastewater," 20th Edition; Edited by L. S. Clesceri et al.; American Public Health Association; 1998, Title, copyright and Table of Contents 23 pages.

\* cited by examiner

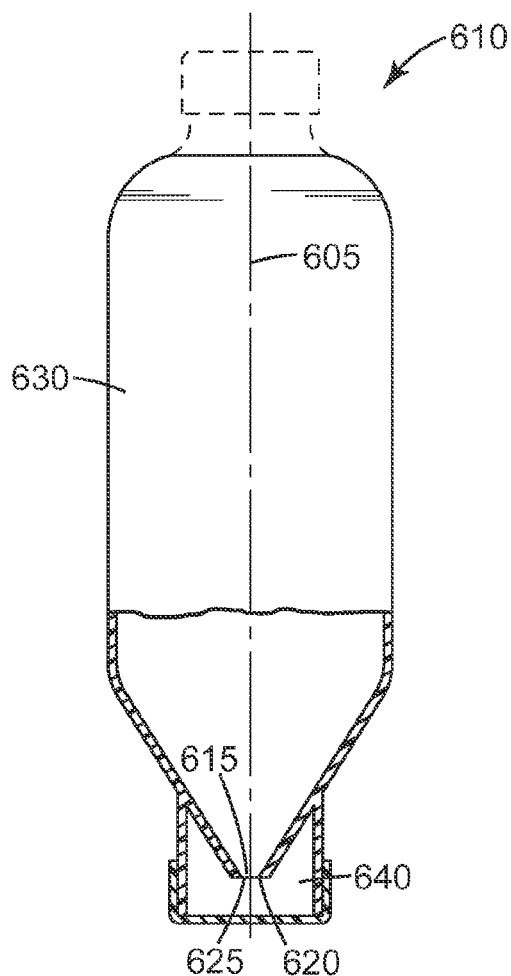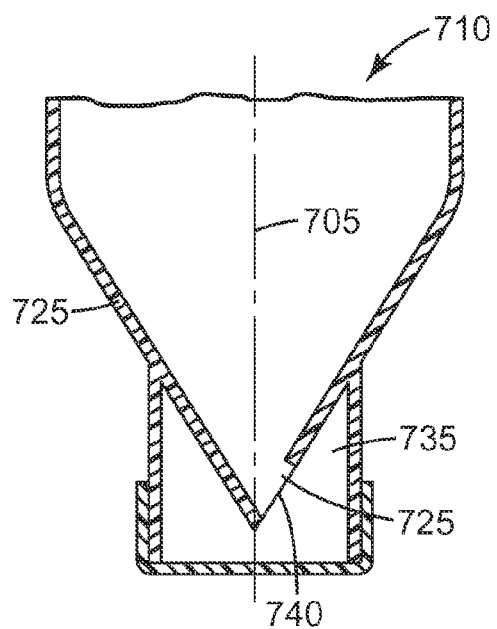
Fig. 6
Fig. 7

SAMPLING DEVICES AND METHODS FOR CONCENTRATING MICROORGANISMS

CROSS REFERENCE TO RELATED APPLICATION

This application claims the benefit of U.S. Provisional Patent Application No. 61/141,900, filed Dec. 31, 2008.

FIELD

The present disclosure relates to sampling devices and methods for concentrating microorganisms using such devices.

BACKGROUND

Food-borne illnesses and hospital-acquired infections resulting from microorganism contamination are a concern in numerous locations all over the world. Thus, it is often desirable or necessary to assay for the presence of bacteria or other microorganisms in various clinical, food, environmental, or other samples, in order to determine the identity and/or the quantity of the microorganisms present.

Bacterial DNA or bacterial RNA, for example, can be assayed to assess the presence or absence of a particular bacterial species even in the presence of other bacterial species. The ability to detect the presence of a particular bacterium, however, depends, at least in part, on the number of the bacterium in the sample being analyzed. Bacterial samples can be plated or cultured to increase the numbers of the bacteria in the sample to ensure an adequate level for detection, but the culturing step often requires substantial time and therefore can significantly delay the assessment results.

Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or non-magnetic particles). Such methods, however, have tended to be expensive and still somewhat slower than desired for at least some diagnostic applications.

Concentration methods that are not strain-specific have also been used (for example, to obtain a more general assessment of the microorganisms present in a sample). After concentration of a mixed population of microorganisms, the presence of particular strains can be determined, if desired, by using strain-specific probes.

Non-specific concentration or capture of microorganisms has been achieved through methods based upon carbohydrate and lectin protein interactions. Chitosan-coated supports have been used as non-specific capture devices, and substances (for example, carbohydrates, vitamins, iron-chelating compounds, and siderophores) that serve as nutrients for microorganisms have also been described as being useful as ligands to provide non-specific capture of microorganisms. Various inorganic materials (for example, hydroxyapatite and metal hydroxides) have been used to non-specifically bind and concentrate bacteria.

Physical concentration methods (for example, filtration, chromatography, centrifugation, and gravitational settling) have also been utilized for non-specific capture, with and/or without the use of inorganic binding agents. Such non-specific concentration methods have varied in speed, cost (at least some requiring expensive equipment, materials, and/or trained technicians), sample requirements (for example, sample nature and/or volume limitations), space requirements, ease of use (at least some requiring complicated multi-step processes), suitability for on-site use, and/or effectiveness.

SUMMARY

The present disclosure describes a method for concentrating microorganisms with a concentration agent in a sampling device. More specifically, methods for concentrating microorganisms from large volume samples in the presence of concentration agents in such devices can provide for rapid, low cost, simple (involving no complex equipment or procedures), and/or effective processes for concentrating microorganisms.

In one aspect, a method is provided for concentrating microorganisms. The method includes providing a unitary sampling device comprising a first reservoir, a second reservoir and a passageway having a first opening in communication with the first reservoir and a second opening in communication with the second reservoir, wherein fluid can flow between the two reservoirs through the passageway. The entire volume of the first reservoir is above the first opening when the unitary sampling device is in an upright position, and the entire volume of the second reservoir is not above the second opening when the unitary sampling device is in any position. The second reservoir has at least one resealable external opening. The method includes mixing a concentration agent and a sample comprising a microorganism in the unitary sampling device to provide a microorganism bound composition. The method also includes inverting the unitary sampling device such that the second reservoir is oriented substantially above the first reservoir for collecting a major portion of the microorganism bound composition from the second reservoir.

In one aspect, a unitary sampling device is provided. The unitary sampling device comprises a first reservoir having a first opening, a second reservoir having a second opening and at least one resealable external opening. The unitary sampling device also includes a passageway connecting the first reservoir to the second reservoir. The passageway having the first opening is in communication with the first reservoir and the second opening is in communication with the second reservoir. The entire volume of the first reservoir is above the first opening when the unitary sampling device is in an upright position. The entire volume of the second reservoir is not above the second opening when the unitary sampling device is in any position.

In one aspect, a method for concentrating microorganisms is provided. The method includes providing a dual component sampling device comprising a first reservoir having a main body, a resealable external opening and a first end shaped so that it is narrower at the part most distal from the main body. The most distal part of the first end has a first connector connected to a detachable aspirable second reservoir having a second connector. The first reservoir is oriented substantially above the detachable aspirable second reservoir. The first connector is capable of attaching to the second connector so that fluid can flow between the two reservoirs. The method includes mixing a concentration agent and a sample comprising a microorganism in the dual component sampling device to provide a microorganism bound composition. The method also includes directing the microorganism bound composition from the first end of the first reservoir into the detachable aspirable second reservoir.

In one aspect, a dual component sampling device is described. The dual component sampling device comprises a first reservoir having a main body, a resealable external opening and a first end shaped so that it is narrowest at the part most distal from the main body. The most distal part has a first connector. The dual component sampling device includes a detachable aspirable second reservoir having a second connector. The first connector attaches to the second connector so that fluid can flow between the first reservoir and the detachable aspirable second reservoir.

In one aspect, a method for concentrating microorganisms is provided. The method includes providing a unitary sampling device comprising a first reservoir having a first opening and at least one resealable external opening, and a second reservoir having a second opening. The unitary sampling device also includes an element comprising a housing and a movable feature residing within the housing, and a second external opening. The movable feature has at least a first location and a second location. The interior of the second reservoir is located within the movable feature and the second opening resides on the exterior or a portion of the movable feature. The first reservoir is located above the element when the unitary sampling device is in an upright position. The second external opening is located below the element when the unitary sampling device is in the upright position. At the first location, a first passageway connects the first reservoir to the second reservoir so that the first opening is in communication with the second opening. At the second location, a second passageway connects the second reservoir to the second external opening so that the second opening is in fluid communication with the second external opening. The method includes mixing a concentration agent and a sample comprising a microorganism in the sampling device to provide a microorganism bound composition. The method also includes transferring the microorganism bound composition from a first location to a second location so that the second opening is in fluid communication with the second external opening.

In one aspect, a unitary sampling device is provided. The unitary sampling device comprises a first reservoir having a first opening and at least one resealable external opening, a second reservoir having a second opening, an element, and a second external opening. The element comprises a housing and a movable feature residing within the housing. The movable feature has at least a first location and a second location. The interior of the second reservoir is located within the movable feature and the second opening resides on the exterior or a portion of the movable feature. The first reservoir is located above the element when the unitary sampling device is in an upright position. The second external opening is located below the element when the unitary sampling device is in the upright position. At the first location, the first passageway connects the first reservoir to the second reservoir so that the first opening is in fluid communication with the second opening. At the second location, the second passageway connects the second reservoir to the second external opening so that the second opening is in fluid communication with the second external opening.

In one aspect, a method for concentrating microorganism is provided. The method includes providing a unitary sampling device comprising a first reservoir having a first opening, a first resealable external opening and a first volume. The unitary sampling device comprises a second reservoir having a second opening, a second external opening and a second volume. The unitary sampling device also comprises a plunger having a seal. The seal resides on a portion of the plunger proximate to a distal end of the plunger. The seal isolates the second volume of the second reservoir from the first volume of the first reservoir. The second volume is removed through the second external opening, and the first reservoir is located above the second reservoir when the sampling device is in an upright position. The method includes mixing a concentration agent and a sample comprising a microorganism in the unitary sampling device to provide a microorganism bound composition. The method also includes transferring the microorganism bound composition located in the second reservoir through the second external opening with the plunger.

In one aspect, a unitary sampling device is provided. The unitary sampling device comprises a first reservoir, a second reservoir, and a plunger. The first reservoir has a first opening, a first resealable external opening and a first volume. The second reservoir has a second opening, a second external opening and a second volume. The plunger has a seal. The seal resides on a portion of the plunger proximate to a distal end of the plunger. The seal traps the second volume of the second reservoir from the first volume of the first reservoir. The second volume is removed through the second external opening, and the first reservoir is located above the second reservoir when the sampling device is in an upright position.

BRIEF DESCRIPTION OF THE DRAWINGS

FIG. 6 is a schematic representation of a unitary sampling device of FIG. 2 having a passageway centered on an axis extending from the center of the first reservoir to the center of the second reservoir.

FIG. 7 is a schematic representation of a unitary sampling device of FIG. 2 having a passageway not centered on an axis extending from the center of the first reservoir to the center of the second reservoir.

DETAILED DESCRIPTION

Figure 1:
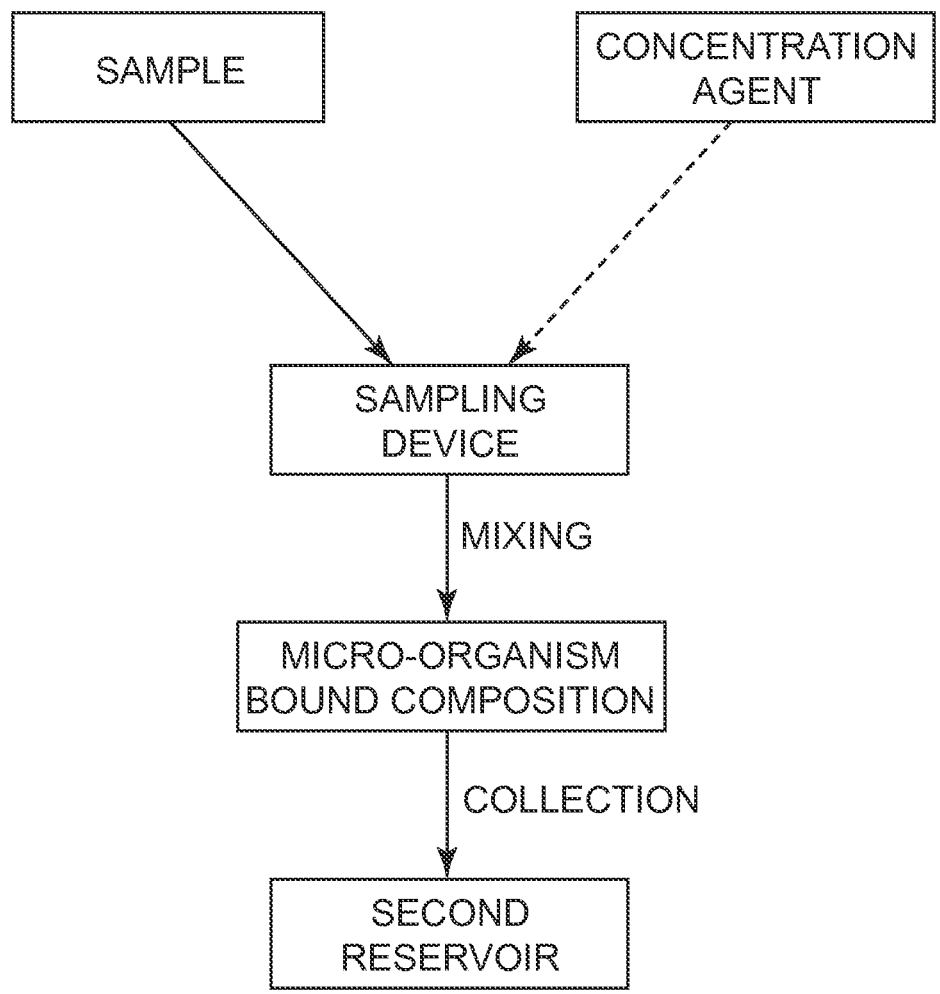
FIG. 1 is a schematic representation of a method for concentrating microorganisms.

Although the present disclosure is herein described in terms of specific embodiments, it will be readily apparent to those skilled in the art that various modifications, rearrangements, and substitutions can be made without departing from the spirit of the invention. The scope of the present invention is thus only limited by the claims appended herein.

The recitation of numerical ranges by endpoints includes all numbers subsumed within that range (e.g., 1 to 5 includes 1, 1.5, 2, 2.75, 3, 3.8, 4, and 5).

As included in this specification and the appended claims, the singular forms "a", "an", and "the" include plural referents unless the content clearly dictates otherwise. Thus, for example, reference to a composition containing "a compound" includes a mixture of two or more compounds. As used in this specification and appended claims, the term "or" is generally employed in its sense including "and/or" unless the content clearly dictates otherwise.

Unless otherwise indicated, all numbers expressing quantities or ingredients, measurement of properties and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present disclosure. At the very least, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains errors necessarily resulting from the standard deviations found in their respective testing measurements.

The present disclosure describes methods for concentrating microorganisms from large volume samples. A unitary sampling device having a first reservoir and a second reservoir is provided for mixing a concentration agent and a sample comprising a microorganism for forming a microorganism bound composition. A dual component sampling device is also described. The concentration agent concentrates at least a portion of the microorganisms present in the sample. The microorganism bound composition is collected in a second reservoir of the sampling device.

Unitary sampling devices having an integrated (e.g., one piece construction) first reservoir and a second reservoir are provided. Similarly, dual component sampling devices described herein refer to a two component device having an independent first reservoir and an independent second reservoir (e.g., detachable first and second reservoirs). The first reservoir and the second reservoir can be connected to form the dual component sampling device. The first reservoir of the sampling devices typically has a larger volume than the volume of the second reservoir. The second reservoir is useful for collecting smaller volume samples containing the microorganism bound compositions.

Sampling devices described herein provide for rapid and efficient collection of large volume samples having low microorganism concentrations. In some examples, such sampling devices can be sealed, opened for containing a large volume sample, and then resealed for concentrating microorganisms present in the samples. Concentration agents are added to the sampling devices for mixing with the samples and forming microorganism bound compositions. The sampling devices of the present application described here are compact, portable (e.g., use in field environments), and disposable thus eliminating the possibility of contamination between samples.

Current techniques, for example, such as membrane filtration and centrifugation, are used for obtaining a direct count of microorganisms from large volume samples. However, these methods for microbiological analysis of samples such as water are generally expensive multistep procedures, require sophisticated equipment, and highly trained personnel. Additionally, operational requirements for membrane filtration or centrifugation techniques make these techniques difficult to perform on-site (e.g., in a field environment).

Methods for enumerating microorganism in water samples are described in, for example, "Standard Methods for the Examination of Water and Wastewater (SMEWW), 21$^{st}$ Edition, American Public Health Association, the American Water Works Association, and the Water Environment Federation. Such methods and water quality testing regulations stipulate testing 100 ml sample volumes which can not be easily performed in a field environment.

FIG. 1 is a process flow diagram for concentrating microorganism by the methods described herein. As illustrated in FIG. 1, a large volume sample comprising microorganisms is added to a sampling device. The large volume sample is mixed with a concentration agent in the sampling device to form a microorganism bound composition. The microorganism bound composition in then collected in the second reservoir. In some embodiments, the concentration agent can be added to the sampling device before the addition of the sample comprising microorganisms. In some embodiments, the concentration agent can be added to the sampling device after the addition of the sample comprising microorganisms. In some embodiments, the sampling device can contain a concentration agent for efficient and portable use in field applications. At the site of sample acquisition, the sampling device having the concentration agent can be opening for delivery and containment of the sample. After the microorganism bound composition has been formed from mixing the concentration agent and the sample, the microorganism bound composition can be collected for further analyses.

Each of the sampling devices described herein provide a first reservoir and a second reservoir. The first reservoir is designed to accommodate a large volume sample having sufficient volume for mixing of the sample and the concentration agent to form the microorganism bound composition. Microorganism bound compositions can be, for example, dispersible in the sample, and then collected or transferred from the first reservoir to the second reservoir of the sampling device. The second reservoir has a smaller volume than the first reservoir in order to contain the microorganism bound composition.

Figure 2:
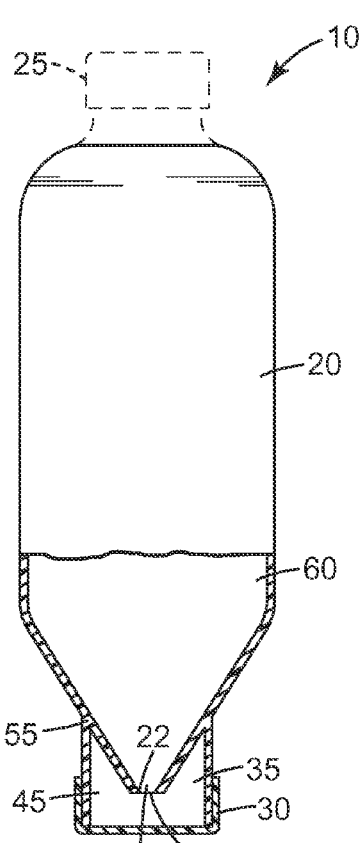
FIG. 2 is a schematic representation of a unitary sampling device having a first reservoir, a second reservoir and a passageway.

FIG. 2 illustrates a unitary sampling device 10. Unitary sampling device 10 comprises a first reservoir 20, a second reservoir 35, a passageway 40 and a resealable external opening 30. An opening 25 adjacent to the first reservoir 20 is optional. The first reservoir 20 is connected to the second reservoir 35 at an interface 55 providing the unitary structure. Both the first reservoir 20 and the second reservoir 35 have a volume. The first reservoir 20 has a first volume 60 and the second reservoir 35 has a second volume 45. Passage way 40 has a first opening 22 in communication with the first reservoir 20 and a second opening 27 in communication with the second reservoir 35. The first reservoir 20 contacts the second reservoir 35 at an interface 55.

In some embodiments, a sample comprising at least one microorganism can be added to the unitary sampling device 10 of FIG. 2 via the resealable external opening 30. A concentration agent can be added to the sample within the unitary sampling device 10, or the concentration agent can be present in the unitary sampling device 10 prior to the addition of the sample. The sample and the concentration agent can be mixed in the first reservoir 20 of the unitary sampling device 10 in an upright position, such that the entire volume of the first reservoir 20 is above the first opening 22 to provide the microorganism bound composition. The microorganism bound composition can, for example, settle from the first reservoir 20 through the passageway 40 into the second reservoir 35. The unitary sampling device 10 can be inverted so that the second reservoir is oriented substantially above the first reservoir. At least a major portion of the microorganism bound composition can be collected in the second volume 45 of the second reservoir 35. The unitary sampling device 10 provides for efficient transfer of the microorganism bound composition from the first reservoir 20 to the second reservoir 35.

Figure 3:
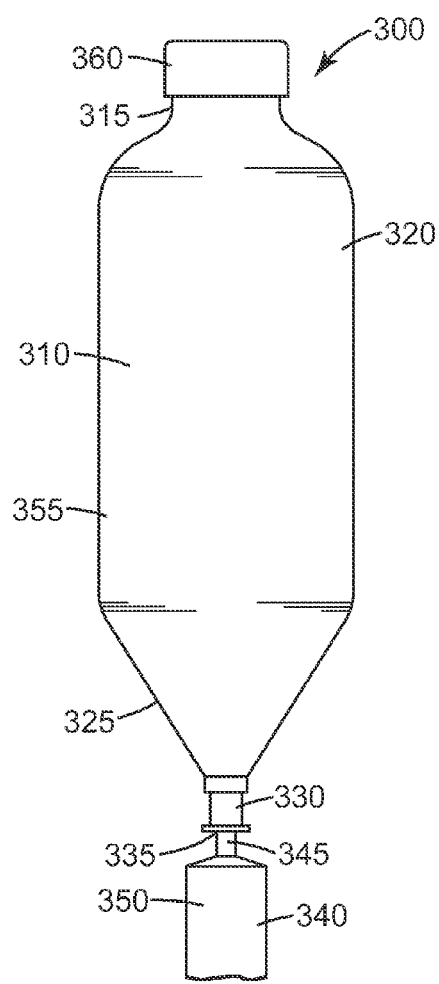
FIG. 3 is schematic representation of a dual component sampling device having a first reservoir and a detachable aspirable second reservoir.
Figure 4:
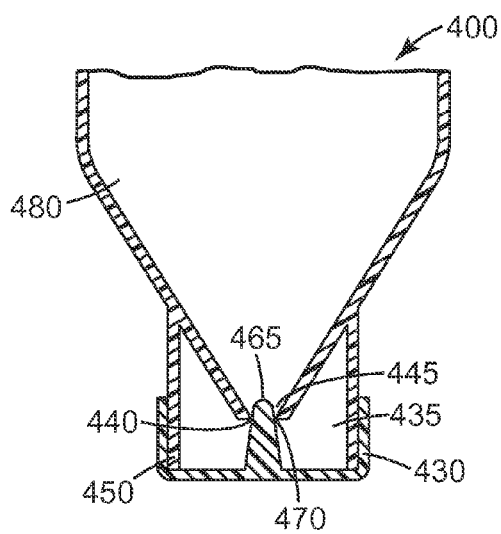
FIG. 4 is a schematic representation of a unitary sampling device of FIG. 2 having a resealable external opening equipped with a closure having a protrusion extending into a passageway.

Dual component sampling device 300 is illustrated in FIG. 3. Dual component sampling device 300 comprises a first reservoir 320 oriented substantially above a detachable aspirable second reservoir 340. The first reservoir 320 has a main body 355, a resealable external opening 315, a first end 325, a first volume 310, and a first connector 330. The first connector 330 is attached to the detachable aspirable second reservoir 340 at an intersection 335. The detachable aspirable second reservoir 340 has a second volume 350 and a second connector 345 in contact with the first connector 330 of the first reservoir 320 residing at the intersection 335.

In some embodiments, a sample comprising a microorganism can be added to the dual component sampling device 300 at the resealable external opening 360 of FIG. 3. A concentration agent can be added to the dual component sampling device 300 prior to or after the addition of the sample. The sample and the concentration agent can be mixed in the first reservoir 320 to provide the microorganism bound composition. In some embodiments, the microorganism bound composition can travel through the sample within the main body 355 by gravity, for example, to the first end 325 of the first reservoir 320. The first connector 330 of the first reservoir 320 can be connected to the detachable aspirable second reservoir 340 at the second connector 345 at intersection 335. The microorganism bound composition can be directed from the first end 325 to the detachable aspirable second reservoir 340 via the conical shape of the first end 325 of the first reservoir 320. A known volume of the microorganism bound composition can be collected in the detachable aspirable second reservoir 340 for further analyses.

FIG. 4 illustrates one embodiment of a unitary sampling device 400. The second reservoir 435 has a resealable external opening 450 comprising a closure 430 having a protrusion 465. The protrusion 465 extends through passageway 440 from the second opening 470 to the first opening 445 when the closure 430 is attached to the resealable external opening 450. The protrusion 465 is selected to prevent the microorganism bound compositions from re-entering first reservoir 480 after inverting the unitary sampling device 400 and collecting such microorganism bound compositions in the second reservoir 435.

In some embodiments, the protrusion 465 can isolate the first reservoir 480 from the second reservoir 435 prior to the addition of the sample and/or the concentration agent. In some embodiments, the protrusion 465 can be used to isolate a least a portion of a microorganism bound composition within the second reservoir 435 from the first reservoir 480. The protrusion 465 can reduce or prevent the microorganism bound composition from flowing through the first opening 445 via the passageway 440 and through the second opening 470 of the unitary sampling device 400.

FIG. 5 illustrates one embodiment of a unitary sampling device 500. The second reservoir 535 has a resealable external opening 550 comprising a closure 530 having a protrusion 565. The protrusion 565 extends from the closure 530 in proximity of the second opening 570 without extending into the passageway 540 when the closure 530 is attached to the resealable external opening 550. The protrusion 565 is selected to at least partially block microorganism bound compositions from re-entering first reservoir 580 after inverting the unitary sampling device 500 and collecting the microorganism bound compositions in the second reservoir 535.

In some embodiments, the protrusion 565 can partially isolate the first reservoir 580 from the second reservoir 535. After mixing the concentration agent and a sample comprising a microorganism in the unitary sampling device 500, the unitary sampling device 500 can be inverted so that the second reservoir 535 is oriented substantially above the first reservoir 580. During the inverting step, the protrusion 565 of the closure 530 can direct at least a portion of the microorganism bound composition into the second reservoir 535 for collection.

FIG. 6 illustrates one embodiment of a unitary sampling device 610. The passageway 620 of the unitary sampling device 610 comprises a first opening 615 and a second opening 625. The passageway 620 is centered on an axis 605 extending from the center of the first reservoir 630 to the second reservoir 640.

In some embodiments, passageway 620 of unitary sampling device 610 of FIG. 6 can provide for flow of a microorganism bound composition from the first reservoir 630 at the first opening 615 through passageway 620 to the second opening 625 of the second reservoir 640. The unitary sampling device 610 can be inverted so that the second reservoir 640 is oriented above the first reservoir 630 so that at least a major portion of the microorganism bound composition can collect in the second reservoir 640.

FIG. 7 illustrates one embodiment of a unitary sampling device 710. The passageway 740 of the unitary sampling device 710 comprises a first opening 715 and a second opening 725. Passageway 740 is not centered on axis 705 extending from the center of the first reservoir 725 to the second reservoir 735.

In some embodiments, passageway 740 of unitary sampling device 710 of FIG. 7 can provide for flow of a microorganism bound composition from the first reservoir 725 through passageway 740 being not centered (e.g., off-centered) on axis 705. The unitary sampling device 710 can be inverted so that the second reservoir 735 is oriented above the first reservoir 725 so that at least a major portion of the microorganism bound composition can collect in the second reservoir 735.

FIG. 8 illustrates a unitary sampling device 800. Unitary sampling device 800 comprises a first reservoir 810, a second reservoir 850, an element 820, and a second external opening 880. The first reservoir 810 has a first opening 860 and at least one resealable external opening 890. The second reservoir 850 has a second opening 870. The element 820 comprises a housing 830 and a movable feature 840 residing within the housing 830. The movable feature 840 has a first location where a first passageway connects the first opening 860 to the second opening 870 such that second reservoir 850 is in fluid communication with the first reservoir 810. The interior of the second reservoir 850 is located within the movable feature 840 and the second opening 870 resides on the exterior of a portion of the movable feature 840. The first reservoir 810 is located above the element 820 when the unitary sampling device 800 is in an upright position.

In some embodiments, the second reservoir 850 of unitary sampling device 800 can have a first location for containing at least a portion of a microorganism bound composition. The second reservoir 850 typically has a fixed volume to collect the microorganism bound composition. The movable feature 840 containing the second reservoir 850 can be rotated to select a location between the first reservoir 810 and the second reservoir 850.

Figure 9:
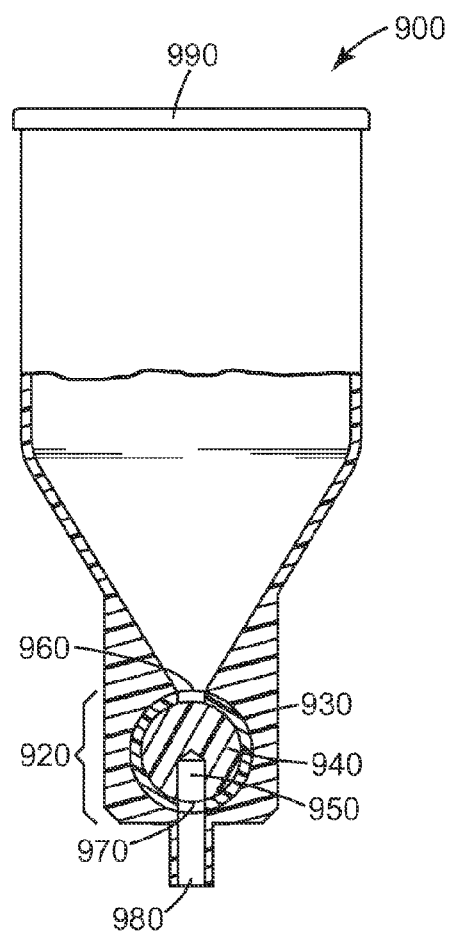
FIG. 9 is a schematic representation of a unitary sampling device of FIG. 8; the unitary sampling device illustrated at a second location.

FIG. 9 illustrates a unitary sampling device 900 comprising a first reservoir 910, a second reservoir 950, an element 920 and a second external opening 980. The first reservoir 910 has a first opening 960 and at least one resealable external opening 990. The second reservoir 950 has a second opening 970. The element 920 comprises a housing 930 and a movable feature 940 residing within the housing 930. The movable feature 940 has a second location where a second passageway connects the second reservoir 950 to the second external opening 980 so that the second opening 970 is in fluid communication with the second external opening 980.

In some embodiments, the second reservoir 950 residing within the movable feature 940 of the unitary sampling device 900 can have a second location so that a fixed volume of the microorganism bound composition retained within the second reservoir 950 can be transferred via a second passageway. The second passageway at the second location connects the second reservoir 950 to the second external opening 980 for delivery of the microorganism bound composition from the second reservoir 950.

Figure 10:
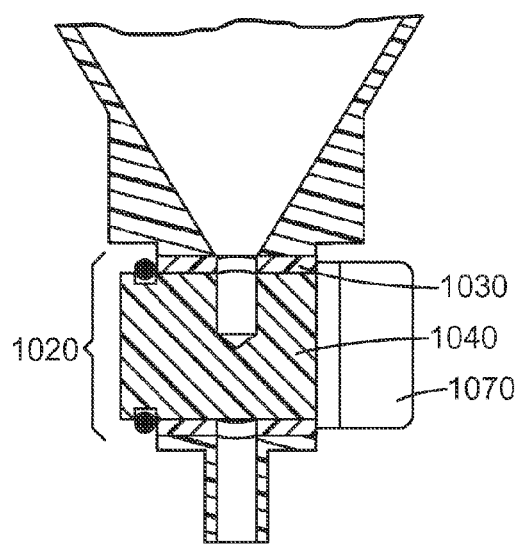
FIG. 10 is a schematic representation of a side view of the element of FIG. 8.

FIG. 10 illustrates a side view of element 1020. Element 1020 has a housing 1030 and a movable feature 1040. Movable feature 1040 has a first component 1070 for moving the second reservoir from a first location to a second location (not shown). In some embodiments, the first component 1070 protrudes from the movable feature 1040 for accessability to the movable feature 1040.

Figure 11:
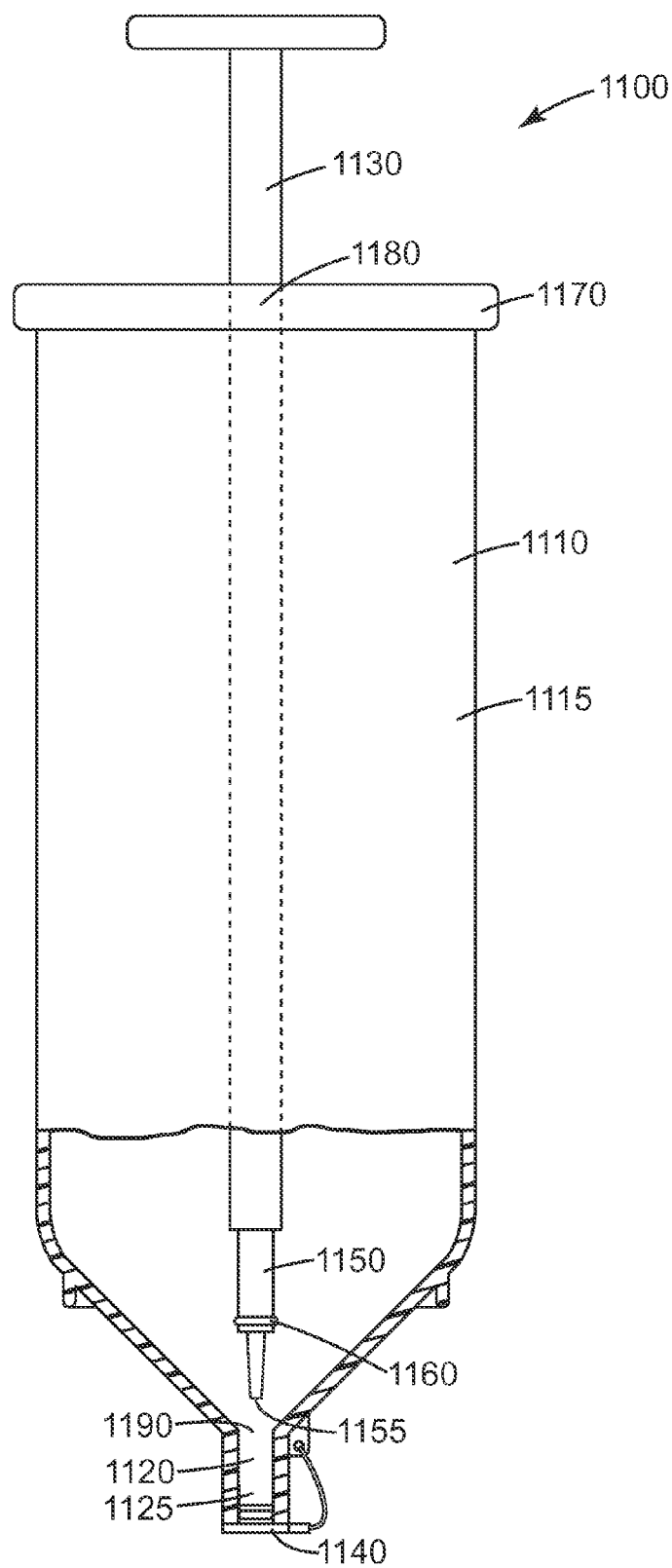
FIG. 11 is a schematic representation of a unitary sampling device having a first reservoir, a second reservoir, and a plunger. The plunger positioned above the second reservoir.

FIG. 11 illustrates a unitary sampling device 1100. Unitary sampling device 1100 comprises a first reservoir 1110, a second reservoir 1120, and a plunger 1130. The first reservoir 1110 has a first opening 1190, a first resealable external opening 1170, and a first volume 1115. The second reservoir 1120 has a second external opening 1140, and a second volume 1125. The plunger 1130 has a seal 1160 residing on a portion of the plunger 1130 proximate to a distal end 1155. The seal 1160 isolates the second volume 1125 of the second reservoir 1120 from the first volume 1115 of the first reservoir 1110. The second volume 1125 can be removed from the second reservoir 1120 through the second external opening 1140. The first reservoir 1110 is located above the second reservoir 1120 when the unitary sampling device 1100 is in an upright position.

In some embodiments, the unitary sampling device 1100 can be utilized with a base or a clamp for supporting and/or positioning the unitary sampling device 1100 in an upright position. In some embodiments, the base and/or clamp can be used to hold the unitary sampling device 1100 in a stationary position. Similarly, the base or clamp can be removed from the unitary sampling device 1100 for portability.

Figure 12:
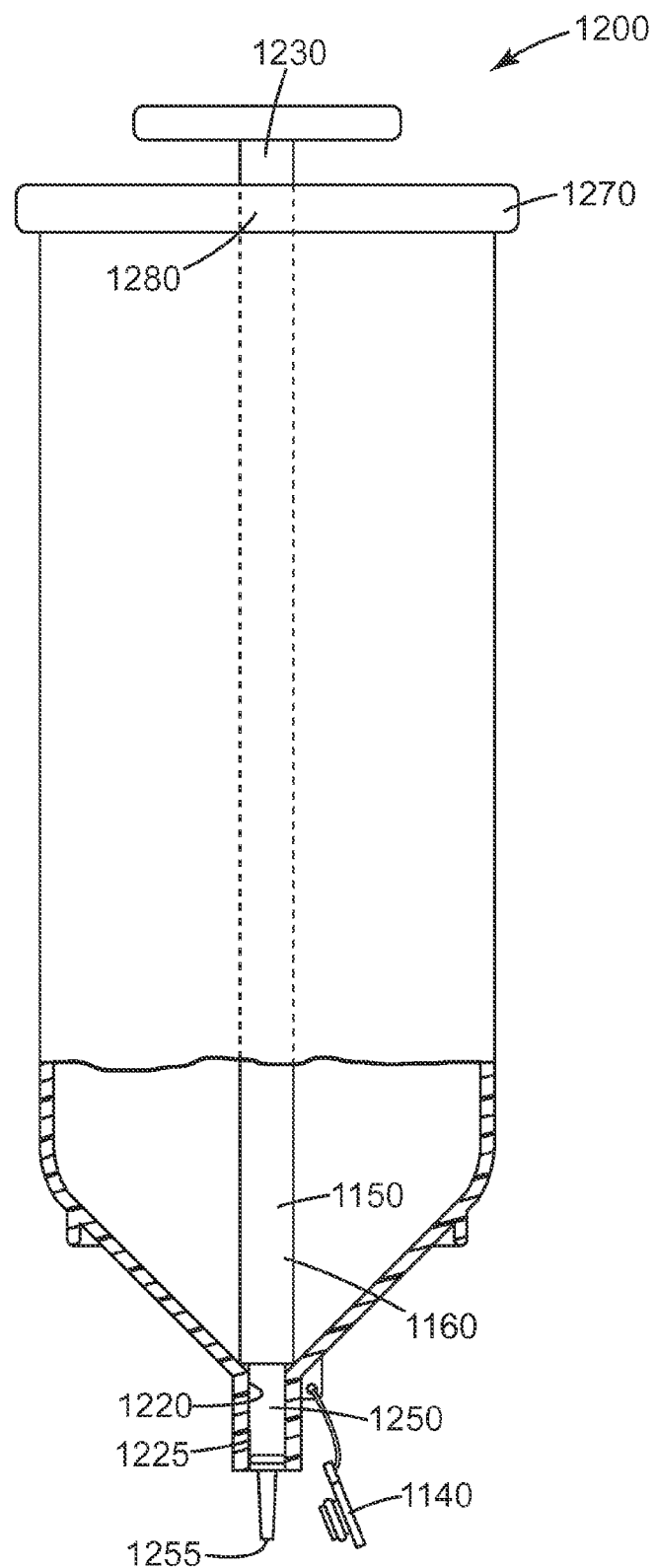
FIG. 12 is a schematic representation of the unitary sampling device of FIG. 11 having the plunger extending through the second reservoir.

FIG. 12 illustrates a unitary sampling device 1200. Unitary sampling device 1200 comprises a first reservoir 1210, a second reservoir 1220, and a plunger 1230. The plunger 1230 having the seal 1260 can be moved to displace the second volume 1225 of the second reservoir 1220. The distal end 1255 of plunger 1230 can extend below the second reservoir 1220 and the second external opening 1240.

The sampling devices illustrated in FIGS. 2-12 of the present disclosure can be formed from a number of materials. Materials useful for forming the sampling devices can include, for example, glass, polymeric materials, composite materials, and the like. These devices can also be constructed of more than one material. Some examples of polymeric materials include polypropylene, polycarbonate, acrylics, polystyrene, polyolefin, high density polyethylene, high density polypropylene, and the like. In some embodiments, devices can be formed from one or more methods of fabrication including, for example, injection molding, blow molding, and by other fabrication techniques.

Concentration agents suitable for mixing with samples comprising a microorganism for providing microorganism bound compositions are described. Concentration agents are generally particulate or dispersible in the sample, and also concentrate microorganisms present in large volume samples. Such concentration agents have been found effective for capturing microorganisms. The term "concentration agent" generally refers to a material for concentrating a general population of microorganisms present in a sample. Examples of concentration agents have been described in U.S. Patent Application Nos. 60/912,711; 60/977180; 60/977,171; 60/977,188; and U.S. Patent Application Publication No. 2007/0269341, each of which is incorporated herein by reference in its entirety.

Concentration or capture using concentration agents (e.g., capture agents), in some embodiments, can be selected to be nonspecific or specific to any particular strain, species, or type of microorganism and therefore provide for the concentration of a general population of microorganisms in a sample. In some embodiments, specific strains of microorganisms can be detected from among the captured microorganism population using any known detection method with strain-specific probes or with strain-selective culture media. Thus, the concentration agents can be used, for example, in the detection of microbial contaminants or pathogens (particularly water-borne and food-borne pathogens such as bacteria) in clinical, food, environmental, or other samples.

In carrying out the method of the present disclosure, the concentration agents can be used in any form that is amenable to sample contact and microorganism capture (for example, in particulate form or applied to a support such as a dipstick, film, filter, tube, well, plate, beads, membrane, or channel of a microfluidic device, or the like). Preferably, the concentration agents are used in particulate form, more preferably comprising microparticles (preferably, microparticles having a particle size in the range of about 1 micrometer (more preferably, about 2 micrometers) to about 100 micrometers (more preferably, about 50 micrometers; even more preferably, about 25 micrometers; most preferably, about 15 micrometers; where any lower limit can be paired with any upper limit of the range).

Concentration agents useful for carrying out the method of the present disclosure include particulate concentration agents that comprise metal, metal oxide microparticles, metal silicates, diatomaceous earth, surface modified diatomaceous earth, particles having functional groups, biomolecules, fragments of biomolecules, nanoparticles, and combinations thereof.

Some examples of concentration agents include iron, silica, titania, zirconia and others useful for collecting and concentrating samples. In some embodiments, gamma-FeO(OH) (also known as lepidocrocite) can be used as a concentration agent. Such concentration agents have been found to be more effective than other iron-containing concentration agents in capturing gram-negative bacteria, which are the microorganisms of greatest concern in regard to food- and water-borne illnesses and human bacterial infections. The concentration agents can further include (in addition to gamma-FeO(OH)) other components (for example, boehmite ($\alpha$-AlO(OH)), clays, iron oxides, and silicon oxides), but, preferably, such other components do not significantly interfere with the intimate contact of the sample and the concentration agent when carrying out the method of the present disclosure. Gamma-FeO(OH) is also commercially available (for example, from Alfa Aesar, A Johnson Matthey Company, Ward Hill, Mass., and from Sigma-Aldrich Corporation, St. Louis, Mo.).

In carrying out the method of the present disclosure, the concentration agents can be used in particulate form, more preferably comprising microparticles (preferably, microparticles having particle sizes (largest dimension) in the range of about 3 micrometers (more preferably, about 5 micrometer; most preferably, about 10 micrometers) to about 100 micrometers (more preferably, about 80 micrometers; even more preferably, about 50 micrometers; most preferably, about 35 micrometers; where any lower limit can be paired with any upper limit of the range). Preferably, the particles are agglomerates of smaller particles. The particles preferably comprise crystallites that are less than about 1 micrometer in size (preferably, less than about 0.5 micrometer in size). The crystallites can be present as acicular crystallites, as raft-like structures comprising acicular crystallites, or as combinations of the acicular crystallites and raft-like structures. The concentration agents preferably have a surface area as measured by the BET (Brunauer-Emmett-Teller) method (calculation of the surface area of solids by physical adsorption of nitrogen gas molecules) that is greater than about 25 square meters per gram ($m^2/g$), more preferably greater than about 50 $m^2/g$, and most preferably greater than about 75 $m^2/g$.

The preferred agglomerated form of such particles can provide adsorptive capabilities of fine particle systems without the handling and other hazards often associated with fine particles. In addition, such agglomerate particles can settle readily in fluid and thus can provide rapid separation of microorganisms from a fluid phase (as well as allowing low back pressure if used in filtration applications).

In some embodiments, metal silicates can be used as concentration agents. Particularly useful metal silicates with a surface composition having a metal atom to silicon atom ratio of less than or equal to about 0.5, as determined by X-ray photoelectron spectroscopy (XPS). Preferably, the surface composition also comprises at least about 10 average atomic percent carbon, as determined by X-ray photoelectron spectroscopy (XPS). XPS is a technique that can determine the elemental composition of the outermost approximately 3 to 10 nanometers (nm) of a sample surface and that is sensitive to all elements in the periodic table except hydrogen and helium. XPS is a quantitative technique with detection limits for most elements in the 0.1 to 1 atomic percent concentration range. Preferred surface composition assessment conditions for XPS can include a take-off angle of 90 degrees measured with respect to the sample surface with a solid angle of acceptance of ±10 degrees.

When dispersed or suspended in water systems, metal silicates can exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). The concentration agents used in carrying out the method of the present disclosure have zeta potentials that are more negative than that of, for example, a common metal silicate such as ordinary talc. Yet the concentration agents are more effective than talc in concentrating microorganisms such as bacteria, the surfaces of which generally tend to be negatively charged. Preferably, the concentration agents have a negative zeta potential at a pH of about 7 (more preferably, a Smoluchowski zeta potential in the range of about −9 millivolts to about −25 millivolts at a pH of about 7; even more preferably, a Smoluchowski zeta potential in the range of about −10 millivolts to about −20 millivolts at a pH of about 7; most preferably, a Smoluchowski zeta potential in the range of about −11 millivolts to about −15 millivolts at a pH of about 7).

Examples of useful metal silicates include amorphous silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form (more preferably, amorphous, spheroidized metal silicates; most preferably, amorphous, spheroidized magnesium silicate). Metal silicates are known and can be chemically synthesized by known methods or obtained through the mining and processing of raw ores that are naturally-occurring.

Amorphous, at least partially fused particulate forms of metal silicates can be prepared by any of the known methods of melting or softening relatively small feed particles (for example, average particle sizes up to about 25 microns) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle), the description of which is incorporated herein by reference). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, as 3M Cosmetic Microspheres CM-111, available from 3M Company, St. Paul, Minn.).

In some embodiments, amorphous metal silicates can further comprise other materials including oxides of metals (for example, iron or titanium), crystalline metal silicates, other crystalline materials, and the like, provided that the concentration agents have the above-described surface compositions. The concentration agents, however, preferably contain essentially no crystalline silica.

In some embodiments, diatomaceous earth bearing, on at least a portion of its surface, a surface treatment comprising a surface modifier comprising titanium dioxide, fine-nanoscale gold or platinum, or a combination thereof for use as concentration agents.

Thus, concentration agents comprising certain types of surface-treated or surface-modified diatomaceous earth (namely, bearing a surface treatment comprising a surface modifier comprising titanium dioxide, fine-nanoscale gold or platinum, or a combination thereof) can be effective when compared to untreated diatomaceous earth for concentrating microorganisms. The surface treatment preferably further comprises a metal oxide selected from ferric oxide, zinc oxide, aluminum oxide, and the like, and combinations thereof (more preferably, ferric oxide). Although noble metals such as gold have been known to exhibit antimicrobial characteristics, the gold-containing concentration agents used in the process of the invention surprisingly can be effective not only in concentrating the microorganisms but also in leaving them viable for purposes of detection or assay.

Useful surface modifiers include fine-nanoscale gold; fine-nanoscale platinum; fine-nanoscale gold in combination with at least one metal oxide (preferably, titanium dioxide, ferric oxide, or a combination thereof); titanium dioxide; titanium dioxide in combination with at least one other (that is, other than titanium dioxide) metal oxide; and the like; and combinations thereof. Preferred surface modifiers include fine-nanoscale gold; fine-nanoscale platinum; fine-nanoscale gold in combination with at least ferric oxide or titanium dioxide; titanium dioxide; titanium dioxide in combination with at least ferric oxide; and combinations thereof.

More preferred surface modifiers include fine-nanoscale gold; fine-nanoscale platinum; fine-nanoscale gold in combination with ferric oxide or titanium dioxide; titanium dioxide; titanium dioxide in combination with ferric oxide; and combinations thereof (even more preferably, fine-nanoscale gold; fine-nanoscale gold in combination with ferric oxide or titanium dioxide; titanium dioxide in combination with ferric oxide; and combinations thereof). Fine-nanoscale gold, fine-nanoscale gold in combination with ferric oxide or titanium dioxide, and combinations thereof are most preferred. In some embodiments, useful concentration agents (e.g., dispersible particles) can have binding groups bound to such particles. The binding (e.g., functional) groups of the particles can have a specific affinity for specific microorganisms present in the samples. In some embodiments, the binding groups having more than site available for attaching multiple microorganisms present in a sample.

In some embodiments, the particles have magnetic properties. The particles can, for example, have magnetic cores. Microorganism bound compositions containing such concentration agents can be collected by the application of a magnetic field, for example, to transfer the composition from the first reservoir to the second reservoir of a sampling device.

In some embodiments, biomolecules (e.g., antibodies) can be covalently bonded to particles by any of a variety of methods for forming concentration agents. For example, glutaraldehyde, aldehyde-Schiff base, n-hydroxyl succinimide, azlactone, cyanogen bromide, maleic anhydride, etc., may be used as suitable attachment chemistries.

The biomolecule-binding group can be functionalized with various chemical groups that allow for binding to a biomolecule. Such groups are typically provided by biomolecule-binding compounds represented by the formula A-L-B. The biomolecule-binding group B may be any useful functional group capable of reacting and forming a covalent bond (preferably a nonreversible covalent bond) with any of the biomolecules of interest. A wide variety of such groups is known and may be useful. Generally the group B will be different from the group A (surface-bonding group). In this representation, L can be a bond or any of a variety of organic linkers. Organic linkers L can be linear or branched alkylene, arylene, or a combination of alkylene and arylene groups, optionally including heteroatoms. For certain embodiments, the L groups do not include divalent alkylene oxide-containing oligomeric or polymeric groups. For certain embodiments, if the L groups do include divalent alkylene oxide-containing oligomeric or polymeric groups that could provide shielding and/or water-dispersible characteristics to the nanoparticles, they are not the only shielding and/or water-dispersible groups present on the nanoparticles.

Nonlimiting examples of such reactive groups B include those selected from the group consisting of amines (particularly primary amines, although secondary amines can also be used, which can be aromatic and/or aliphatic), hydrazines, hydroxyl groups (—OH), sulfones, aldehydes, alcohols (—OR), oxiranes (such as ethylene oxides), halides (Cl, Br, I, F), N-oxysuccinimides, acrylates, acrylamides, alpha,beta-ethylenically or acetylenically unsaturated groups with electron withdrawing groups (e.g., alpha,beta-unsaturated ketones), carboxylates, esters, anhydrides, carbonates, oxalates, aziridines, epoxy groups, N-substituted maleimides, azlatones, and combinations thereof.

Examples of certain of these B groups with L linkers attached are shown below, wherein the B groups include aldehyde and hydroxyl groups, halides, esters, hydrazines (aliphatic or aromatic), and N-oxysuccinimides:

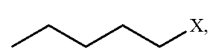

X = CHO, OH

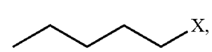

X = I, Br, Cl, F 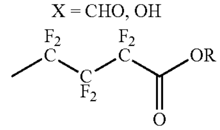 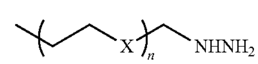 n = 0-30

X = CH2, O, S, NH, NR (R = alkyl)

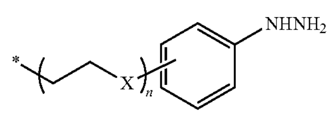

and n = 0-10

X = CH2, O, S, NH, NR (R = alkyl)

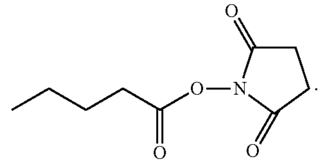

In some embodiments, vinyl sulfones, epoxy groups, acrylates, and amines are preferred as they allow for direct attachment without complicated reaction chemistry (as is needed with, for example, carboxylates). The following are representations of preferred B groups with L linkers, wherein the B groups include vinyl sulfone, epoxy, acrylate, and amine groups:

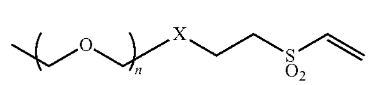

n = 0-15

X = NH, NR, S, O 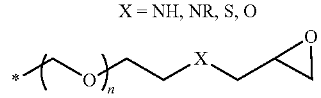 n = 0-15

X = CH2, O, S 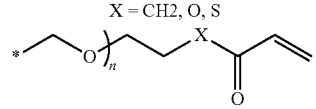 n = 0-15

X = CH2, O, NH, NR, S

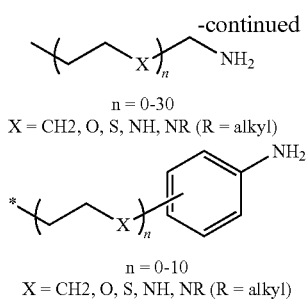

n = 0-30
X = CH2, O, S, NH, NR (R = alkyl)

n = 0-10
X = CH2, O, S, NH, NR (R = alkyl)

Various combinations of the biomolecule-binding groups can be used. They can be on the same particle or on different particles.

In some embodiments, biomolecule-binding groups are those that are hydrolysis resistant. Hydrolysis resistant functional groups for reaction with biomolecules include acrylates, alpha,beta-unsaturated ketones, a N-sulfonyldicarboximide derivative, an acylsulfonamide, a N-sulfonylaminocarbonyl, a fluorinated ester, a cyclic azlactone, a sulfonyl fluoride, a cyclic oxo-carbon acid (deltic, squaric, croconic and rhodizonic), a cyanuric fluoride, a vinyl sulfone, a perfluorinated phenol, and various combinations thereof.

For biomolecule-binding compounds A-L-B, the surface-bonding groups A are typically silanols, alkoxysilanes, or chlorosilanes, which can be monofunctional, difunctional, or trifunctional. For example, the silanol groups on the surfaces of the silica nanoparticles are reacted with at least one silanol, alkoxysilane, or chlorosilane group of a biomolecule-binding compound to form a functionalized nanoparticle.

For certain embodiments, the biomolecule-binding groups include alpha,beta-ethylenically or acetylenically unsaturated group with an electron withdrawing group. Nonlimiting examples of electron withdrawing groups include carbonyls, ketones, esters, amides, —SO₂—, —SO—, —CO—CO—, —CO—COOR, sulfonamides, halides, trifluoromethyl, sulfonamides, halides, maleimides, maleates, or combinations thereof. For certain embodiments, the electron withdrawing groups is a ketone, ester, or amide.

The biomolecule-binding groups can be provided by biomolecule-binding compounds represented by the formula A-L-B. The biomolecule-binding group B is an alpha,beta-ethylenically or acetylenically unsaturated group. Generally, the group B will be different from the group A (surface-bonding group). In this representation, L can be a bond or any of a variety of organic linkers, such that certain preferred group L-B (or simply B) has the following structures:

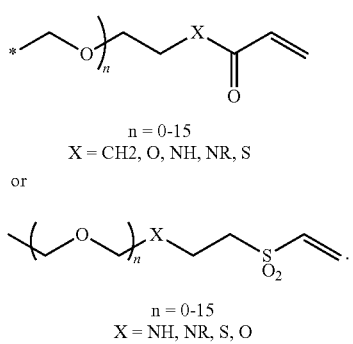

n = 0-15
X = CH2, O, NH, NR, S or n = 0-15
X = NH, NR, S, O

In certain embodiments the biomolecule-binding group is an acrylate or an alpha,beta-unsaturated ketone. Acrylates and alpha,beta-unsaturated ketones exhibit the desirable properties of stability in water over a wide range of pH and yet also exhibit high reactivity with primary amines to irreversibly form a Michael addition adduct.

A Michael addition adduct can result when an amino-group-bearing-biomolecule covalently bonds to a biomolecule-binding group by means of a carbon-nitrogen bond involving an amino group of the biomolecule and the beta position of an alpha,beta-ethylenically unsaturated group bearing a carbonyl unit at alpha position.

In some embodiments, acrylates and alpha,beta-unsaturated ketones can be used since they are compatible with a wide variety of surface-bonding groups. In certain embodiments, the acrylate is multifunctional. Examples of biomolecule-binding compounds include N-(3-acryloxy-2-hydroxypropyl) 3-aminopropyl triethoxysilane, 3-acryloxypropyl trimethoxysilane, vinyl sulfone triethoxysilane-2,1,1,2-trifluorovinyl, 1,1,2-trichlorovinyl, 1,1-dichlorovinyl, 1,1-difluorovinyl, 1-fluoro or 1-chlorovinyl silanes, alpha,beta-unsaturated containing silanes, silane-containing quinones. Those of ordinary skill in the art will recognize that a wide variety of other biomolecule-binding compounds are useful in the present disclosure as compounds that can be used to functionalize particles with biomolecule-binding groups. Preferably, a sufficient amount of biomolecule-binding compound is reacted on the surface of such particles to provide the desired level of attachment of biomolecule of interest (a polypeptide such as an antibody, preferably an IgG antibody).

In some embodiments, the biomolecule-binding group can include an amine and/or a hydrazine. The amine and/or hydrazine may be aromatic, aliphatic, or a combination thereof. The amine may be primary or secondary, although it is preferably a primary amine, the more preferred primary amines are hydrophilic amines including poly(ethylene oxide) amines and polyimines.

In some embodiments, the biomolecule-binding group can include an aryl amine and/or an aryl hydrazine. The amine may be primary or secondary (i.e., nontertiary), although it is preferably a primary amine. In such embodiments, the biomolecule-binding groups can be provided by biomolecule-binding compounds represented by the formula A-L-B, wherein the biomolecule-binding group B is an aryl nontertiary amine and/or aryl hydrazine group. Generally, the group B will be different from the group A (surface-bonding group). In this representation, L can be a bond or any of a variety of organic linkers, such that certain preferred groups L-B (or simply B) have the following structures:

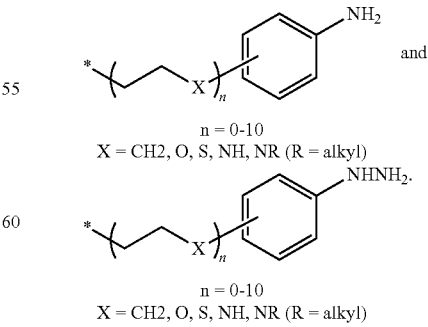

n = 0-10
X = CH2, O, S, NH, NR (R = alkyl)

and n = 0-10
X = CH2, O, S, NH, NR (R = alkyl)

In some embodiments, the B groups can include an aryl amine and/or aryl hydrazine and reacts with a biomolecule having a free carbonyl group through a Schiff base mechanism, thereby forming a linkage of the formula —Ar—N═C(H)-biomolecule, or —Ar—NHN═C(H)-biomolecule wherein Ar is an aryl group, which may be unsubstituted or substituted. The aryl group may include a single aromatic ring or multiple aromatic rings, which may or may not include heteroatoms (particularly, S, N, O). Examples include naphthalene, anthracene, pyrene, and biphenyl. If the aryl group is substituted, the substituents (e.g., hydroxyl, carboxyl, methoxy, methyl, amino groups) should not interfere sterically or electronically with the function of the aryl amine and/or aryl hydrazine as the biomolecule-binding group.

The size of the aryl group should be balanced against the number and type of water-dispersible groups to avoid excessive agglomeration of the nanoparticles. If desired, the aryl group can be substituted with hydrophilic groups to assist in the dispersion of the particles.

In some embodiments, examples of biomolecule-binding compounds (i.e., compounds capable of providing a biomolecule-binding group having an aryl amine and/or aryl hydrazine group), represented by the formula A-L-B, can include 4-aminophenyltrimethoxy silane.

Preferably, a sufficient amount of biomolecule-binding compound can be reacted with the particles so as to provide the desired level of attachment of biomolecule of interest (e.g., an oxidized polypeptide such as an oxidized antibody, preferably an IgG antibody).

In some embodiments, biomolecule-binding groups can include primary aliphatic and/or aromatic amines, and the biomolecule-binding groups having a biomolecule covalently bonded thereto include a biotin-containing group covalently bonded to the surface of the particles through the amine-functionalized groups.

In some embodiments, amine-containing biomolecule-binding groups can be aromatic amines. As aliphatic amines, they generally have no less than about 6 carbon atoms, particularly when the water-dispersible and/or shielding groups include poly(alkylene oxide)-containing groups.

In some embodiments, biomolecules useful as concentration agents can be any chemical compound that naturally occurs in living organisms, as well as derivatives or fragments of such naturally occurring compounds. Biomolecules consist primarily of carbon and hydrogen, along with nitrogen, oxygen, phosphorus, and sulfur. Other elements sometimes are incorporated but are much less common. Biomolecules include, but are not limited to, proteins, antibodies, polypeptides, carbohydrates, polysaccharides, lipids, fatty acids, steroids, prostaglandins, prostacyclines, vitamins, cofactors, cytokines, and nucleic acids (including DNA, RNA, nucleosides, nucleotides, purines, and pyrimidines), metabolic products that are produced by living organisms including, for example, antibiotics and toxins. Biomolecules may also include derivatives of naturally occurring biomolecules, such as a protein or antibody that has been modified with chemicals (e.g., oxidized with sodium periodate). Biomolecules may also include crosslinked naturally occurring biomolecules, or a crosslinked product of a naturally occurring biomolecule with a chemical substance. Thus, as used herein, the term "biomolecule" includes, but is not limited to, both unmodified and modified molecules (e.g., glycosylated proteins, oxidized antibodies) and fragments thereof (e.g., protein fragments). Fragments of biomolecules can include those resulting from hydrolysis due to chemical, enzymatic, or irradiation treatments, for example.

In certain embodiments, biomolecules may be covalently bonded to one or more of the biomolecule-binding groups. In certain embodiments, the biomolecule includes or can be modified to include an aldehyde group prior to its attachment to the biomolecule-binding group.

The attachment of an antibody (e.g., oxidized antibody) or other biomolecule (e.g., oxidized biomolecule) typically takes place under mild conditions, and can occur under a broad pH range, preferably pH at 4-11, more preferably pH at 6-10, and most preferably pH at 7-9. The preferred temperature for attachment of an antibody (e.g., oxidized antibody) or other biomolecule (e.g., oxidized biomolecule) is room temperature. Also, lower or higher temperatures can be used, but not at temperatures which denature the biomolecule. This chemistry is suitable for all kinds of biological media, basic and even mildly acidic buffer solutions, and in mixed solvents including solvents such as DMSO or acetonitrile.

In some embodiments, biomolecules such as biotin can be used to capture target biomolecular analytes (e.g., antibodies). Such amine-containing groups with biotin bonded thereto can be formed by the reaction of (+)-Biotin-N-hydroxy-succinimide ester compounds with a primary aliphatic and/or aromatic amine (the biomolecule-binding group), wherein the amine functional group is bonded to a surface through linking group L. Alternatively, the reaction of (+)-Biotin-N-hydroxy-succinimide ester compounds with the amine can be carried out prior to binding to the surface of the silica nanoparticles.

Biotin, also known as vitamin H or cis-hexahydro-2-oxo-1H-thieno-[3-,4]-imidazole-4-pentanoic acid, is a basic vitamin which is essential for most organisms including bacteria and yeast. Biotin has a molecular weight of 244 daltons, much lower than its binding partners, avidin and streptavidin. Biotin is also an enzyme cofactor of pyruvate carboxylase, trans-carboxylase, acetyl-CoA-carboxylase and beta-methylcrotonyl-CoA carboxylase which together carboxylate a wide variety of substrates. Derivatives of biotin, such as N-hydroxysuccinimide esters of biotin (referred to as NHS-biotin), N-hydroxysulfosuccinimide esters of biotin (referred to as sulfo-NHS-biotin), sulfosuccinimidyl-6-[biotinamido] hexanoate (referred to as sulfo-NHS-LC-biotin), sulfosuccinimidyl-6-[biotinamido]-6-hexanamidohexanoate (referred to as sulfo-NHS-LC-LC-biotin), and N-hydroxysuccinimide $PEG_{12}$-biotins or N-hydroxysuccinimide $PEG_4$-biotins (referred to as NHS—$PEO_{12}$-biotin or sulfo-NHS—$PEO_4$-biotin), can be used to attach to amines on silica nanoparticles. Thus, using this nomenclature, the biotin or biotin derivatives are the biomolecules, whereas the biomolecule-binding groups are the amines. The biotin-containing compound (e.g., biotin or derivatives of biotin) forms a bond with avidin or strepavidin, the complex of which is capable of binding to an antibody, which can be the target analyte or can be specific for a target analyte (e.g., a bacterium).

The selective attachment of a target biological analyte can be achieved directly or it may be achieved through a capture agent, e.g., antigen-antibody binding (where the target biological analyte itself includes the antigen bound to an antibody immobilized on the detection surface).

Concentration agents having capture agents can include species (e.g., molecules, groups of molecules) that have high affinity for a target biological analyte, and preferably are specific for a target analyte. Capture agents include, for example, antibodies and fragments thereof (Fab, Fab', Fc), polypeptides, aptamers, DNA, RNA, oligonucleotides, proteins, antibodies, carbohydrates, polysaccharides, lipids, fatty acids, steroids, vitamins, cytokines, lectins, cofactors, and receptors (e.g., phage receptors). Capture agents may also include derivatives of naturally occurring biomolecules, such as a protein or antibody that has been modified with chemicals. These may also include crosslinked naturally occurring biomolecules, or a crosslinked product of a naturally occurring biomolecule with a chemical substance.

Some biomolecule capture agents suitable for use in the present disclosure include polypeptides including antibodies, antibody conjugates, and proteins such as avidin, streptavidin, and clumping factor). In particular, biomolecule capture agents are antibodies. The term "antibody" is intended to include whole antibodies of any isotype (IgG, IgA, IgM, IgE, etc.), and fragments thereof from vertebrate, e.g., mammalian species, which are also specifically reactive with foreign compounds, e.g., proteins.

The antibodies can be monoclonal, polyclonal, or combinations thereof. Antibodies can be fragmented using conventional techniques and the fragments screened for utility in the same manner as whole antibodies. Thus, the term includes segments of proteolytically cleaved or recombinantly prepared portions of an antibody molecule that are capable of selectively reacting with a certain protein. Nonlimiting examples of such proteolytic and/or recombinant fragments include Fab, F(ab')$_2$, Fv, and single chain antibodies (scFv) containing a VL and/or VH domain joined by a peptide linker. The scFv's can be covalently or non-covalently linked to form antibodies having two or more binding sites. Antibodies can be labeled with any detectable moieties known to one skilled in the art. In some aspects, the antibody that binds to an analyte one wishes to measure (the primary antibody) is not labeled, but is instead detected indirectly by binding of a labeled secondary antibody or other reagent that specifically binds to the primary antibody.

The surface coverage and packing of the capture agent on the surface of the concentration agent may affect the sensitivity of detecting the target biological analyte. The immobilization chemistry that links the capture agent to the surface may play a role in the packing of the capture agents, preserving the activity of the capture agent, and may also contribute to the reproducibility and shelf-life of the surfaces. A variety of immobilization methods described elsewhere herein may be used in connection with surfaces to achieve the goals of high yield, activity, shelf-life, and stability.

Bioaffinity pairs, such as antigen/hapten, antibody/antigen binding fragment of the antibody, or complementary nucleic acids, bioreceptor/ligand (interleukin-4 and its receptor) may be used to attach capture agents. One of the pairs of such biomolecules is covalently attached to the biomolecule-binding agent. These biomolecules form part of a "capture agent" for a target biological analyte. For example, the strong bond formed between biotin and avidin and/or streptavidin may be particularly useful when attaching an antibody to a surface. Preferably, streptavidin can be used as a means to attach an antibody, to a surface. Streptavidin is a tetrameric protein isolated from *Streptomyces avidinii* that binds tightly to the vitamin biotin. Proteins, such as streptavidin, can be attached to surfaces through a number of chemistries.

Derivatives of biotin, such as N-hydroxysuccinimide esters of biotin (referred to as NHS-biotin), N-hydroxysulfosuccinimide esters of biotin (referred to as sulfo-NHS-biotin), sulfosuccinimidyl-6-[biotinamido]hexanoate (referred to as sulfo-NHS-LC-biotin), sulfosuccinimidyl-6-[biotinamido]-6-hexanamidohexanoate (referred to as sulfo-NHS-LC-LC-biotin), and N-hydroxysuccinimide PEG$_{12}$-biotins, and N-hydroxysuccinimide PEG$_4$-biotins (referred to as NHS—PEO$_{12}$-biotin or sulfo-NHS-PEO$_4$-biotin), can be used to attach biotins to biomolecules, such as antibodies, at primary amino acid groups. These biotinylated biomolecules can subsequently be attached to a surface that has streptavidin attached thereto.

"Target biological analytes" include, for example, tissues, cells, or biomolecules therewithin or derived therefrom (e.g., organism-specific antigens, enzymes, or other proteins, peptides, carbohydrates, toxins, or prions, cell wall components or fragments, flagella, pili, nucleic acids, antibodies).

As used herein, the term "tissue" refers to multicellular aggregates or an organ derived from animals or plants, and includes both viable and nonviable cells, connective tissue, and interstitial fluids. "Cell" refers to the basic structural and functional unit of all living organisms, including animals, plants, and single-celled microorganisms.

Concentration agents useful in the method of the present disclosure can be applied to a variety of different types of samples comprising microorganisms. Samples having low microorganism concentrations can have microorganisms within the sample concentrated as described herein. Some examples of samples can include, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), environmental surfaces (e.g., floors, walls, ceilings, fomites, equipment, water, water containers, and air filters), a laboratory, or an area that has been potentially subjected to bioterrorism. Food processing, handling, and preparation area samples, potable water and environmental surfaces are preferred, as these are often of particular concern in regard to food supply contamination by bacterial pathogens.

A sample useful in the method of the present disclosure can be in the form of a fluid (e.g., a liquid, or a dispersion or suspension). In some embodiments, samples obtained in the form of a liquid can be concentrated with a dispersible concentration agent so that microorganism bound composition can be formed.

Examples of samples that can be used (either directly or after treatment to provide a fluid sample) in carrying out the process of the invention include foods (for example, fresh produce rinsates or ready-to-eat lunch or "deli" meats), beverages (for example, juices or carbonated beverages), potable water, and biological fluids (for example, whole blood or a component thereof such as plasma, a platelet-enriched blood fraction, a platelet concentrate, or packed red blood cells); cell preparations (e.g., dispersed tissue, bone marrow aspirates, or vertebral body bone marrow); cell suspensions; urine, saliva, and other body fluids; bone marrow; spinal fluid; and the like, as well as lysed preparations, such as cell lysates, which can be formed using known procedures such as the use of lysing buffers, and the like. Preferred samples include foods, beverages, potable water, biological fluids, environmental samples, and combinations thereof (with foods, beverages, potable water, environmental samples, and combinations thereof being more preferred).

Sample volume of the sampling device can vary, depending upon the particular application. For example, when the method of the present disclosure is used for clinical diagnostic or research application, the volume of the sample can typically be in a range from about 0.5 milliliters to about 10 milliliters. When the method is used for food pathogen testing assay or for potable water safety testing, the volume of the sample can typically be in the milliliter to liter range (for example, 100 milliliters to 3 liters). In an industrial application, such as bio-processing or pharmaceutical formulation, the sample volume can be tens of thousands of liters.

The process of the invention can isolate microorganisms from a sample in a concentrated state using a concentration agent, and can also allow the isolation of low levels of microorganisms from sample matrix components that can inhibit detection procedures that are to be used. In all of these cases, the process of the invention can be used in addition to, or in replacement of, other methods of microorganism concentration. Thus, optionally, cultures can be grown from samples either before or after carrying out the process of the present disclosure, if additional concentration is desired.

A variety of samples comprising microorganisms can be concentrated as microorganism bound compositions, and collected (e.g., transferred) by one of the methods described herein using the sampling devices of the present disclosure. Microorganisms present in the samples for providing the microorganism bound compositions can include, for example, fungi, yeasts, protozoans, viruses, and the like, and combinations thereof. In some embodiments, the microorganisms can include gram-negative bacteria, gram-positive bacteria, and combinations thereof. The method of concentrating microorganisms using the sampling devices described herein has utility for concentrating and detecting pathogens, which can be important for food safety or for medical, environmental, or anti-terrorism reasons. The process can be particularly useful in the detection of pathogenic bacteria (for example, both gram negative and gram positive bacteria), as well as various yeasts, molds, and mycoplasmas (and combinations of any of these). As used herein, the term "microorganism" refers to prokaryotic or eukaryotic organisms that are generally classified as bacteria, viruses, yeast, filamentous fungi, and protozoa. As used herein, the term "prokaryotic organism" includes all forms of microorganisms considered to be bacteria including cocci, *bacilli*, spirochetes, sheroplasts, protoplasts, spores, etc.

Microbes (i.e., microorganisms) of particular interest include Gram positive bacteria, Gram negative bacteria, fungi, protozoa, mycoplasma, yeast, viruses. Particularly relevant organisms include members of the family *Enterobacteriaceae*, or genera *Staphylococcus* spp., *Streptococcus* spp., *Pseudomonas* spp., *Clostridium* spp., *Enterococcus* spp., *Esherichia* spp., *Bacillus* spp., *Listeria* spp., *Legionella* spp., *Vibrio* spp., as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA), Vancomycin Resistant *Staphylococcus aureus* (VRSA), Vancomycin Intermediate-resistant *Staphylococcus aureus* (VISA)), *Clostridium difficile*, *S. epidermidis*, *Streptococcus pneumoniae*, *S. agalactiae*, *S. pyogenes*, *Enterococcus faecalis*, Vancomycin Resistant *Enterococcus* (VRE), *Bacillus anthracis*, *Bacillus amyloliquefaciens*, *Bacillus amylolyticus*, *Bacillus cereus*, *Bacillus coagulans*, *Bacillus macerans*, *Bacillus megaterium*, *Bacillus polymyxa*, *Bacillus stearothermophillus*, *Bacillus subtilis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Vibrio cholera*, *V. parahemolyticus*, *Salmonella cholerasuis*, *S. typhi*, *S. typhimurium*, *Candida albicans*, *C. glabrata*, *C. krusei*, Strep A, Strep B, *Agrobacterium tumefaciens*, *Alcaligenes xylosoxydans* subsp. denitrificans, *Sphingomonas paucimobilis*, and multiple drug resistant Gram negative rods (MDR).

Such microbes or other species of interest can be analyzed in a test sample that may be derived from any source, such as a physiological fluid, e.g., blood, saliva, ocular lens fluid, synovial fluid, cerebral spinal fluid, pus, sweat, exudate, urine, mucous, lactation milk, or the like. Further, the test sample may be derived from a body site, e.g., wound, skin, nares, scalp, nails, etc.

Besides physiological fluids, other test samples may include other liquids as well as solid(s) dissolved in a liquid medium. Samples of interest may include process streams, water, soil, plants or other vegetation, air, surfaces (e.g., contaminated surfaces), and the like.

In some embodiments, methods for concentrating microorganisms can be carried out by any of various known or hereafter developed methods for providing contact and/or mixing between two materials, for example, in forming a dispersion. For example, the concentration agent (e.g., as a particulate) can be added to the sample comprising a microorganism, or the sample can be added to the concentration agent within the sampling device. The concentration agent and the sample can be combined in any of a variety of sampling devices described within the present application. Optionally, but preferably, the sampling device is capped, closed, or sealed prior to use so as to reduce contamination prior to the addition of the sample. Similarly, the sampling device used herein is capable of being capped, closed, or sealed after use for containment, storage, and ease of portability.

Suitable sampling devices (e.g., unitary sampling devices or dual component sampling devices) for carrying out the method of the present disclosure can be determined by the size of the sample. Useful sampling devices can vary widely in size and design. In some embodiments, sampling devices can be small having a volume of 0.5 milliliter, or larger, such that the volume of the sampling device can be in a range of 100 milliliters to 3 liters. In some embodiments, the sampling device and the concentration agent that comes into contact with the sample can be sterilized (for example, by controlled heat, ethylene oxide gas, hydrogen peroxide, or radiation) prior to use, in order to reduce or prevent any contamination of the sample that might cause detection errors. The amount of concentration agent that is sufficient to capture or concentrate the microorganisms of a particular sample for successful detection will vary (depending upon, for example, the nature and form of the concentration agent and sample volume) and can be readily determined by one skilled in the art. The capture efficiency (the percent of microorganisms in the sample bound to concentration agent) can generally be increased by allowing increased time for the microorganism to come in contact with the concentration agent. The capture efficiency can also be increased by having a higher concentration of concentration agent, which decreases the mean diffusion distance a microorganism must travel to be captured, leading to a shorter incubation time. Therefore, as a generality, the more concentration agent added, the shorter incubation time necessary to capture the same amount of microorganisms. In some embodiments, for example, 10 milligrams of concentration agent for every milliliter of sample can be useful for some applications. For other applications, concentration agents in the range of 1-50 milligrams per milliliter of sample can be utilized.

If desired, contacting or mixing within the sampling device can be effected by passing concentration agents at least once through a sample (for example, by relying upon gravitational settling or by other methods over a period of time. Contact can be enhanced by mixing (for example, by stirring, shaking, or use of a rocking platform) such that the particles of concentration agent repeatedly pass or settle through a substantial portion of the sample. For small volumes on the order of microliters (typically less than 10 milliliters), mixing can be rapid such as by vortexing or "nutation," for example as described in U.S. Pat. No. 5,238,812 (Coulter et al.), the description of which is incorporated herein by reference. For larger volumes on the order of greater than or equal to 1 milliliter (typically 1 milliliter to 3 liters), mixing can be achieved by gently tumbling the concentration agent and the sample in an "end over end" fashion, for example as described in U.S. Pat. No. 5,576,185 (Coulter et al.), the description of which is incorporated herein by reference. Contacting can be carried out for a desired period (for example, for sample volumes of about 100 milliliters or less, up to about 60 minutes of contacting can be useful; preferably, about 15 seconds to about 10 minutes or longer; more preferably, about 15 seconds to about 5 minutes).

Thus, in carrying out the method of the present disclosure, mixing (for example, agitation, rocking, or stirring) and optionally incubation can be used in order to increase microorganism contact with the concentration agent. A preferred contacting method includes both mixing (for example, for about 15 seconds to about 5 minutes) and incubating (for example, for about 3 minutes to about 4 hours) a microorganism containing samples with concentration agent. If desired, one or more additives (for example, lysis reagents, nucleic acid capture reagents (for example, magnetic beads), microbial growth media, buffers (for example, to disperse or extract a solid sample), microbial staining reagents, washing buffers (for example, to wash away unbound material), elution agents (for example, serum albumin), surfactants (for example, Triton X-100 nonionic surfactant available from Union Carbide Chemicals and Plastics, Houston, Tex.), mechanical abrasion/elution agents (for example, glass beads), and the like) can be added to the combination of concentration agent and sample.

The microorganism bound composition formed herein can be collected in the second reservoir of the sampling device. Preferably, collecting of the microorganism bound composition can be achieved by relying, at least in part, upon gravitational settling (gravity sedimentation; for example, over a time period of about 5 minutes to about 4 hours). In some embodiments, however, it can be desirable to accelerate collection (for example, by centrifugation or filtration) or to use combinations of any of the collection methods.

Microorganisms that have been captured or bound by the concentration agent described herein forming microorganism bound compositions can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components.

In some embodiments, microorganisms that have been captured or bound by the concentration agent can also be removed from the devices, placed on a culture dish, allowed to grow for a certain period of time and the colonies can be detected by use of bioluminescence reagents and imaging of the plate using an imaging system such as Milliflex® Rapid Microbiology Detection and Enumeration System (Millipore, Bedford, Mass.).

In some embodiments, the microorganism bound composition can be transferred to a suitable reaction cuvette/vessel and directly detected by adding bioluminescent reagents to the vessel. Bioluminescence can be quantified by measuring bioluminescence in a luminometer.

In some applications, the microorganism bound composition within the sampling device can be transferred to a laboratory for detection. For certain applications, microorganism bound compositions can be removed and placed into a sterile container for transport to a laboratory for detection where, the container can be designed to avoid loss of viability of the microorganisms. Optionally, a preservative can be added to the container to maintain the viability of the microorganisms during transport.

In some embodiments, the microorganism bound composition residing in the second reservoir can be analyzed for microorganisms. In some embodiments, the microorganism bound composition can be removed from the second reservoir and analyzed for microorganisms. Analytical techniques useful for detecting such microorganisms of the microorganism bound composition be accomplished, for example, colorimetrically, electrochemically, fluorimetrically, lumimetrically, by culturing, by utilizing an immunoassay, or by utilizing enzyme assays or through genetic analysis.

Sampling devices of the present disclosure provide for convenience and portability as equipped for concentrating low levels of microorganisms in the presence of concentration agents from large volume samples. The sampling devices described herein are inexpensive and recyclable thus eliminating the need for cleaning and sterilizing these devices before and after each use. A known volume of the microorganism bound composition can be collected from the second reservoir and subsequently analyzed for identifying microorganisms present in such samples.

The disclosure will be further clarified by the following non-limiting examples which are exemplary and not intended to limit the scope of the disclosure.

EXAMPLES

Unless otherwise noted, all parts, percentages, and ratios reported in the following examples are on a weight basis, and all reagents used in the examples were obtained, or are available, from the chemical suppliers described below, or can be synthesized by conventional techniques.

Example 1

Unitary Sampling Device

A unitary sampling device illustrated in FIG. 2 was prepared. A 250 milliliter polypropylene centrifuge tube (#430776; Corning Inc., Ithaca, N.Y.) was utilized for the first reservoir. A circular opening (~6 mm) was formed in the narrow end of the tube to form an angled opening. A 50 milliliter polypropylene centrifuge tube (#430921; Corning, Inc., Ithaca, N.Y.) was used for the second reservoir. The 50 ml tube was heated to soften the polypropylene and the 50 ml tube was placed adjacent to the 250 ml tube to form the unitary sampling device of FIG. 2.

Example 2

Dual Component Sampling Device

A dual component sampling device illustrated by FIG. 3 was prepared. A 250 ml centrifuge tube (described above) was utilized for the first reservoir with a 6 mm opening. A 2 mm threaded female luer lock was inserted into the 6 mm opening. The luer lock was attached in position with structural adhesive. A 5 ml polypropylene syringe (detachable aspirable second reservoir) was attached to the luer lock to form the dual component sampling device of FIG. 3.

Example 3

Unitary Sampling Device

A unitary sampling device of FIG. 7 was prepared as described in Example 1 with the exception that the 6 mm circular opening was formed not centered on the axis.

Example 4

Unitary Sampling Device

A unitary sampling device of FIG. 2 was prepared as described in Example 1 with the exception that the second reservoir was formed from a 100 ml centrifuge tube.

Example 5

Unitary Sampling Device

A unitary sampling device of FIG. 2 was prepared as described in Example 1 with the exception that the second reservoir was formed from a 25 ml centrifuge tube.

Example 6

Unitary Sampling Device

Figure 5:
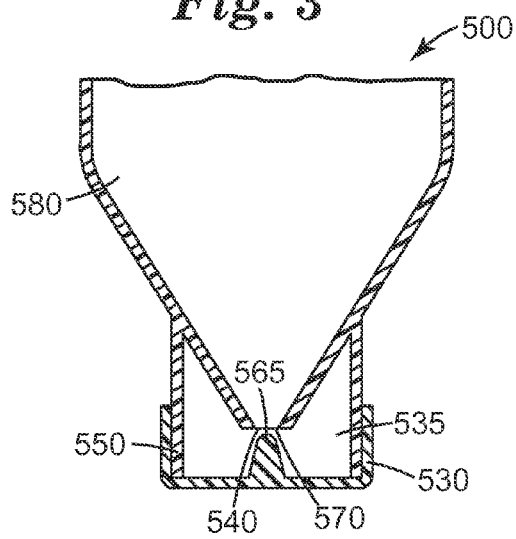
FIG. 5 is a schematic representation of a unitary sampling device of FIG. 2 having a resealable external opening equipped with a closure having a protrusion not extending into the passageway.
Figure 8:
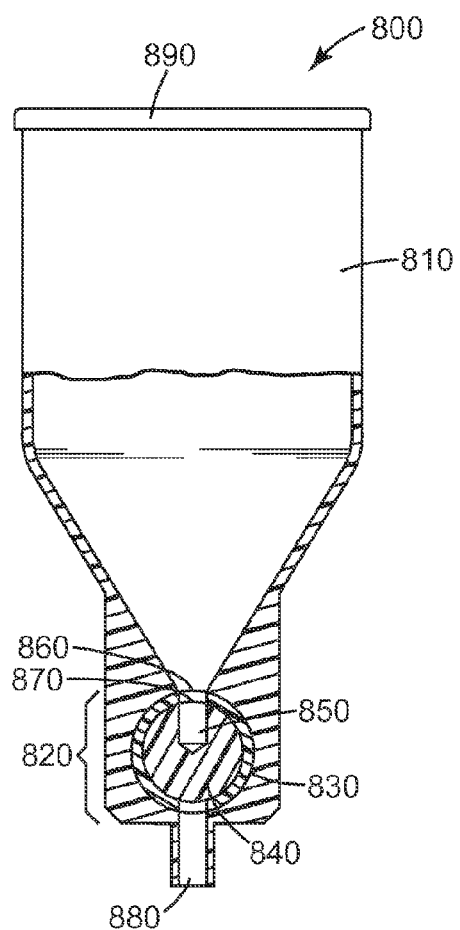
FIG. 8 is a schematic representation of a unitary sampling device having a first reservoir, a second reservoir, an element, and a second external opening. The unitary sampling device illustrated at a first location.

A unitary sampling device of FIG. 2 as described in Example 1 was used. The resealable external opening of the second reservoir was equipped with a closure having a protrusion as illustrated in FIG. 5.

Method for Concentrating Microorganisms using Sampling Devices

An isolated *E. coli* (ATCC 51813) colony was inoculated from a streak plate into 5 ml BBL Trypticase Soy Broth (Becton Dickinson, Sparks, Md.) and incubated at 37° C. for 18-20 hours (overnight culture). The overnight culture at ~$10^9$ colony, having units/ml, was diluted in Butterfield's Buffer (pH 7.2, VWR; West Chester, Pa.). A 1:1000 dilution from a $10^2$ bacteria/ml dilution was prepared in 100 ml of water with a final concentration of 0.1/ml (10 cfus total). One milliliter of a filter sterilized, 100× concentrated adsorption buffer (pH 7.2 containing 5 mM KCl, 1 mM $CaCl_2$, 0.1 mM $MgCl_2$ and 1 mM $K_2HPO_4$) was added.

A concentration agent, 3M microparticles (250 milligrams) (amorphous, spheroidized magnesium silicate X296-Talc; 3M Company, St. Paul, Minn.; U.S. Pat. No. 6,045,913)) was added to each of Examples 1-6 (sampling devices). One hundred milliliters of *E. coli* spiked water was also added to each of the sampling devices. The sampling devices were each sealed with a closure and incubated at room temperature (25° C.) for 60 minutes on a Thermolyne VariMix rocking (mixing) platform at 14 cycles/minute (Barnstead International, Dubuque, Iowa). After the mixing and incubation steps, the sampling devices were not disturbed for 45-60 minutes. Similarly, tubes containing *E. coli* spiked water without the concentration were treated to the same conditions.

In order to collect the microorganism bound composition, the sampling devices (Examples 1, 3-6) were independently inverted so that the composition was collected in the second reservoir. The microorganism bound composition (2-5 milliliters) was pipetted from the second reservoir and transferred to a 15 ml sterile polypropylene tube (VWR, West Chester, Pa.). The microorganism bound composition within their respective tubes was mixed, and pipetted 1 ml at a time onto EC/CC Petrifilm (3M Company, St. Paul, Minn.).

In Example 2, the detachable aspirable second reservoir containing a plunger was drawn to acquire 3-4 ml of the microorganism bound composition to be added to the 15 ml sterile polypropylene tube, and followed by mixing and pipetting 1 ml at a time onto EC/CC Petrifilm.

The petrifilms of Examples 1-6 were processed per the manufacturer's instructions. *E. coli*/Coliform Count was quantified using a EC/CC Petrifilm Plate Reader (3M Company, St. Paul., Minn.). Results for Examples 1-6 were calculated with the formula listed below:

Capture efficiency=(number of colonies from concentration agent on filter/number of colonies in the plated untreated control (no concentration agent))×100

Capture efficiency of *E. Coli* using the sampling devices of Examples 1-6 is illustrated in Table 1. The capture data was obtained from EC/CC Petrifilm on which the retrieved microorganism bound composition was plated.

TABLE 1

Capture of *E coli* from 100 ml water samples

| Example | *E. Coli* in water sample (cfus) | *E. Coli* recovered from concentration agent* (cfus) | Capture Efficiency (percent) |
|---|---|---|---|
| 1 | 12 | 11 | 92 |
| 2 | 13 | 13 | 100 |
| 3 | 12 | 10 | 83 |
| 4 | 13 | 15 | 115 |
| 5 | 13 | 8 | 62 |
| 6 | 11 | 11 | 100 |

*Microorganism bound composition

Various modifications and alterations of this disclosure will be apparent to those skilled in the art without departing from the scope and spirit of this disclosure, and it should be understood that this disclosure is not limited to the illustrative elements set forth herein.

What is claimed is:

1. A method for concentrating microorganisms comprising the steps of:
    providing a sampling device comprising:
        a body comprising
            a first opening at a first end
            a second opening at a second end opposite the first end;
            a first reservoir disposed between the first end and the second end; and
        a rotatable feature disposed in the body between the reservoir and the second opening;
        wherein the rotatable feature comprises a second reservoir;
        wherein the rotatable feature is configured to place the second reservoir into liquid communication with the first reservoir or with the second opening;
        wherein the second reservoir is configured such that it cannot be in simultaneous liquid communication with both the first reservoir and the second opening;
    mixing a concentration agent with a sample comprising a microorganism in the first reservoir to provide a microorganism bound composition; and
    isolating the microorganism bound composition from the first reservoir by rotating the rotatable feature.

2. The method of claim 1, wherein mixing a concentration agent with a sample comprises mixing a concentration agent selected from the group consisting of particles with affinity ligands, particles without affinity ligands, antibodies or antigen binding fragments, receptors and combinations thereof.

3. The method of claim 1, wherein mixing a concentration agent with a sample further comprises mixing a buffer with the concentration agent and the sample.

4. The method of claim 1, wherein the mixing step further comprises mixing a detection agent and a growth medium with the concentration agent and the sample.

5. A sampling device comprising:
- a body comprising
  - a first opening at a first end
  - a second opening at a second end opposite the first end;
  - a first reservoir disposed between the first end and the second end; and
- a rotatable feature disposed in the body between the reservoir and the second opening;
- wherein the rotatable feature comprises a second reservoir;
- wherein the rotatable feature is configured to place the second reservoir into liquid communication with the first reservoir or with the second opening;
- wherein the second reservoir is configured such that it cannot be in simultaneous liquid communication with both the first reservoir and the second opening.

6. The sampling device of claim 5, wherein the first reservoir further comprises a first volume and the second reservoir further comprises a second volume, wherein a ratio of the first volume to the second volume is in a range of about 10:1 to about 1000:1.

7. The sampling device of claim 5, further comprising a concentration agent disposed in the first reservoir, wherein the concentration agent is selected from the group consisting of particles with affinity ligands, particles without affinity ligands, antibodies or antigen binding fragments, receptors and combinations thereof.

8. The sampling device of claim 5, further comprising a detection agent and a growth medium.

9. The sampling device of claim 7, wherein the concentration agent comprises a dispersible or particulate agent.

10. The sampling device of claim 7, wherein the concentration agent comprises gamma-FeO(OH).

11. The sampling device of claim 7, wherein the concentration agent comprises metal silicates.

12. The sampling device of claim 7, wherein the concentration agent comprises diatomaceous earth.

13. The sampling device of claim 7, wherein the concentration agent comprises surface treated diatomaceous earth, the surface treatment selected from the group consisting of titanium dioxide, nanoscale gold, nanoscale platinum and combinations thereof.

* * * * *